(12) United States Patent
Yoo et al.

(10) Patent No.: US 9,640,375 B2
(45) Date of Patent: May 2, 2017

(54) METHOD FOR CRYSTALLIZING LOW MASS IONS FOR DIAGNOSING COLORECTAL CANCER AND METHOD FOR DIAGNOSING COLORECTAL CANCER USING SAME

(75) Inventors: Byong Chul Yoo, Gyeonggi-do (KR); In Hoo Kim, Gyeonggi-do (KR); Kyung Hee Kim, Seoul (KR); Jun Hwa Lee, Gyeonggi-do (KR); Kwang Gi Kim, Seoul (KR); Hee Jin Chang, Seoul (KR); Dae Yong Kim, Gyeonggi-do (KR); Jae Hwan Oh, Seoul (KR); Byung Chang Kim, Gyeonggi-Do (KR); Ji Won Park, Gyeonggi-Do (KR); Sun Young Kim, Seoul (KR)

(73) Assignee: National Cancer Center, Ilsandong-Gu, Goyang-si, Gyeonggi-Do (KR)

( * ) Notice: Subject to any disclaimer, the term of this patent is extended or adjusted under 35 U.S.C. 154(b) by 792 days.

(21) Appl. No.: 13/816,560

(22) PCT Filed: Aug. 12, 2011

(86) PCT No.: PCT/KR2011/005974
§ 371 (c)(1),
(2), (4) Date: Apr. 22, 2013

(87) PCT Pub. No.: WO2012/021042
PCT Pub. Date: Feb. 16, 2012

(65) Prior Publication Data
US 2013/0206977 A1    Aug. 15, 2013

(30) Foreign Application Priority Data

Aug. 12, 2010  (KR) .................. 10-2010-0078017
Oct. 14, 2010  (KR) .................. 10-2010-0100473

(51) Int. Cl.
| | | |
|---|---|---|
| G01N 33/48 | (2006.01) |
| H01J 49/00 | (2006.01) |
| G01N 33/574 | (2006.01) |
| G01N 33/68 | (2006.01) |
| G06F 19/00 | (2011.01) |
| G06G 7/58 | (2006.01) |
| G06F 19/24 | (2011.01) |

(52) U.S. Cl.
CPC .... *H01J 49/0036* (2013.01); *G01N 33/57419* (2013.01); *G01N 33/6848* (2013.01); *G06F 19/703* (2013.01); *G06F 19/24* (2013.01)

(58) Field of Classification Search
CPC .................................. G06F 19/16; G06F 19/24
See application file for complete search history.

(56) References Cited

FOREIGN PATENT DOCUMENTS

WO    2004090550 A2    10/2004

OTHER PUBLICATIONS

Supplementary European Search Report in corresponding European Application No. 11816658.6 dated Feb. 24, 2014.
Kim, Kyung-Hee, et al. "Profiling of Low Mass Ions in Serum from Colorectal Cancer Patients using NALDI-TOF Analysis and Its Application for Chemotherapy Response Prediction." 9th IEEE Conference on Nanotechnology. Jul. 2009, p. 462-464, Genoa, Italy.
Yoo, Byong-Chu, et al. "Identification of Hypoxanthine as a Urine Marker for non-Hodgkin Lymphoma by Low-Mas-Ion Profiling." BMC Cancer, Biomed Central; vol. 10: No. 1, Feb. 23, 2010, p. 55, London, Great Britain.
Lutz, Ursula, et al. "Metabolic Profiling of Glucuronides in Human Urine by LC-MS/MS and Partial Least-Squares Discriminant Analysis for Classification and Prediction of Gender." Analytical Chemistry, vol. 78: No. 13, Jul. 1, 2006, p. 4564-4571.
"MarkerView(TM) Software 1.2.1 for Metabolomic and Biomarker Profiling Analysis—Key Features of MarkerView(TM) Software." Jan. 10, 2010. Retrieved from Internet at :http://www.absciex.com/Documents/Downloads/Literature/mass-spectrometry-cms 042026. pdf.
Kawai, Kazushige, et al. "Hyperfibrinogenemia After Preoperative Chemoradiotherapy Predicts Poor Response and Poor Prognosis in Rectal Cancer." Int. J. Colorectal Dis, vol. 26: No. 1, Sep. 1, 2010, p. 45-51, Berlin, Germany.

*Primary Examiner* — Eric S Dejong

(57) ABSTRACT

The present invention provides a method for determining low mass ions for diagnosing colorectal cancer by using a MALDI-TOF mass spectrometer to biostatistically analyze low mass ions, which are extracted from a biological sample, and a method for providing information for diagnosing colorectal cancer using same. The present inventions can provide a diagnostic method, which requires low cost and a short time for analysis, can analyze large areas, and which can provide superior and credible discriminations.

11 Claims, 37 Drawing Sheets

| CRC | Sex | Age year | Stage | Location | Cell Type | Different -iation | CEA ng/ml |
|---|---|---|---|---|---|---|---|
| CRC-1 | M | 77 | 1 | A-colon | AC | 2 | 1.8 |
| CRC-2 | M | 50 | 1 | Rectum | AC | 1 | 1.9 |
| CRC-3 | F | 47 | 1 | S-colon | AC | 2 | 0.7 |
| CRC-4 | F | 56 | 3 | S-colon | AC | 2 | 1.2 |
| CRC-5 | F | 82 | 1 | A-colon | AC | 1 | 1.1 |
| CRC-6 | M | 59 | 1 | Rectum | AC | 1 | 1.9 |
| CRC-7 | M | 73 | 1 | Rectum | AC | 2 | 3.6 |
| CRC-8 | M | 71 | 1 | S-colon | AC | 1 | 3.6 |
| CRC-9 | M | 50 | 1 | S-colon | AC | 2 | 2.5 |
| CRC-10 | M | 56 | 1 | S-colon | AC | 2 | 7.3 |
| CRC-11 | M | 61 | 1 | Rectum | AC | 2 | 7.7 |
| CRC-12 | F | 78 | 1 | Rectum | AC | 1 | 2.6 |
| CRC-13 | M | 64 | 1 | S-colon | AC | 2 | 1.8 |
| CRC-14 | F | 50 | 1 | Rectum | AC | 2 | 1.6 |
| CRC-15 | F | 59 | 1 | Rectum | AC | 2 | 1.6 |
| CRC-16 | M | 73 | 1 | Rectum | AC | 2 | 1.9 |
| CRC-17 | M | 65 | 1 | S-colon | AC | 2 | 14.0 |
| CRC-18 | M | 72 | 1 | S-colon | AC | 2 | 4.6 |
| CRC-19 | M | 82 | 1 | Rectum | AC | 2 | 3.2 |
| CRC-20 | M | 52 | 3 | S-colon | AC | 1 | 3.2 |
| CRC-21 | F | 59 | 3 | S-colon | AC | 2 | 1.7 |
| CRC-22 | F | 73 | 3 | S-colon | AC | 2 | 5.7 |
| CRC-23 | M | 70 | 3 | S-colon | AC | 2 | 3.6 |

A : Adenoma / AC : Adenocarcinoma /
ASC : Adenosquamous carcinoma /
C : Carcinoid / MAC : Mucinous adenocarcinoma /
SC : Signet-ring cell carcinoma /

FIG. 3A

| CRC | Sex | Age year | Stage | Location | Cell Type | Different -iation | CEA ng/ml |
|---|---|---|---|---|---|---|---|
| CRC-24 | M | 75 | 2 | A-colon | AC | 2 | 2.1 |
| CRC-25 | F | 81 | 2 | S-colon | AC | 1 | 4.1 |
| CRC-26 | F | 76 | 2 | Rectum | AC | 1 | 25.3 |
| CRC-27 | F | 71 | 2 | A-colon | AC | 3 | 1.6 |
| CRC-28 | M | 72 | 2 | A-colon | AC | 2 | 3.8 |
| CRC-29 | F | 82 | 2 | S-colon | AC | 2 | 1.8 |
| CRC-30 | F | 68 | 2 | D-colon | AC | 1 | 1.7 |
| CRC-31 | M | 71 | 2 | S-colon | AC | 2 | 3.6 |
| CRC-32 | F | 67 | 2 | A-colon | AC | 1 | 1.9 |
| CRC-33 | M | 45 | 2 | D-colon | MAC | * | 3.3 |
| CRC-34 | M | 60 | 2 | S-colon | AC | 2 | 2.8 |
| CRC-35 | M | 74 | 2 | S-colon | AC | 2 | 5.3 |
| CRC-36 | M | 57 | 2 | Rectum | AC | 2 | 7.3 |
| CRC-37 | F | 65 | 2 | S-colon | AC | 2 | 2.1 |
| CRC-38 | M | 77 | 2 | A-colon | AC | 1 | 1.5 |
| CRC-39 | M | 71 | 2 | D-colon | AC | 2 | 4.1 |
| CRC-40 | F | 66 | 2 | Rectum | AC | 2 | 4.3 |
| CRC-41 | F | 49 | 2 | A-colon | AC | 1 | 1.6 |
| CRC-42 | F | 79 | 2 | A-colon | AC | 1 | 2.9 |
| CRC-43 | M | 69 | 2 | S-colon | AC | 2 | 4.2 |
| CRC-44 | M | 66 | 2 | S-colon | AC | 2 | 12.0 |
| CRC-45 | M | 74 | 2 | A-colon | AC | 2 | 1.5 |
| CRC-46 | M | 69 | 2 | T-colon | AC | 2 | 1.2 |
| CRC-47 | M | 43 | 2 | S-colon | AC | 2 | 2.2 |

A : Adenoma / AC : Adenocarcinoma /
ASC : Adenosquamous carcinoma /
C : Carcinoid / MAC : Mucinous adenocarcinoma /
SC : Signet-ring cell carcinoma /

FIG. 3B

| CRC | Sex | Age year | Stage | Location | Cell Type | Different -iation | CEA ng/ml |
|---|---|---|---|---|---|---|---|
| CRC-48 | F | 67 | 2 | A-colon | AC | 2 | 1.4 |
| CRC-49 | M | 72 | 2 | A-colon | AC | 1 | 4.9 |
| CRC-50 | F | 67 | 2 | A-colon | AC | 1 | 7.3 |
| CRC-51 | F | 75 | 2 | Rectum | AC | 2 | 12.6 |
| CRC-52 | M | 68 | 2 | D-colon | AC | 2 | 4.7 |
| CRC-53 | F | 60 | 2 | S-colon | AC | 2 | 3.3 |
| CRC-54 | M | 74 | 2 | S-colon | AC | 2 | 9.0 |
| CRC-55 | M | 68 | 3 | A-colon | AC | 1 | 9.2 |
| CRC-56 | F | 55 | 3 | Rectum | AC | 2 | 2.1 |
| CRC-57 | F | 61 | 3 | A-colon | AC | 2 | 12.7 |
| CRC-58 | M | 59 | 3 | S-colon | AC | 2 | 2.7 |
| CRC-59 | M | 67 | 3 | Rectum | AC | 2 | 9.5 |
| CRC-60 | M | 48 | 3 | S-colon | AC | 1 | 1.3 |
| CRC-61 | M | 58 | 3 | Rectum | AC | 2 | 1.7 |
| CRC-62 | F | 50 | 3 | S-colon | AC | 2 | 4.8 |
| CRC-63 | F | 51 | 3 | S-colon | AC | 1 | 7.0 |
| CRC-64 | F | 74 | 3 | T-colon | AC | 2 | 2.5 |
| CRC-65 | M | 60 | 3 | Rectum | AC | 2 | 3.5 |
| CRC-66 | M | 52 | 3 | S-colon | AC | 2 | 2.5 |
| CRC-67 | M | 54 | 3 | A-colon | AC | 1 | 5.3 |
| CRC-68 | M | 82 | 3 | S-colon | AC | 1 | 2.4 |
| CRC-69 | M | 54 | 3 | S-colon | AC | 2 | 5.3 |
| CRC-70 | F | 79 | 3 | Rectum | AC | 2 | 14.1 |
| CRC-71 | F | 44 | 3 | S-colon | AC | 2 | 1.4 |

A : Adenoma / AC : Adenocarcinoma /
ASC : Adenosquamous carcinoma /
C : Carcinoid / MAC : Mucinous adenocarcinoma /
SC : Signet-ring cell carcinoma /

FIG. 3C

| CRC | Sex | Age year | Stage | Location | Cell Type | Differentiation | CEA ng/ml |
|---|---|---|---|---|---|---|---|
| CRC-72 | M | 66 | 3 | Rectum | AC | 2 | 1.2 |
| CRC-73 | M | 53 | 3 | A-colon | AC | 2 | 4.2 |
| CRC-74 | M | 64 | 3 | T-colon | AC | 2 | 1.8 |
| CRC-75 | F | 42 | 3 | S-colon | AC | 2 | 0.8 |
| CRC-76 | M | 49 | 3 | Rectum | AC | 2 | 2.7 |
| CRC-77 | M | 68 | 3 | Rectum | AC | 2 | 3.9 |
| CRC-78 | M | 51 | 3 | S-colon | AC | 2 | 5.2 |
| CRC-79 | M | 64 | 3 | Rectum | AC | 2 | 7.7 |
| CRC-80 | M | 42 | 3 | S-colon | AC | 1 | 2.8 |
| CRC-81 | F | 43 | 3 | A-colon | AC | 2 | 4.7 |
| CRC-82 | M | 66 | 3 | S-colon | AC | 2 | 9.1 |
| CRC-83 | M | 37 | 3 | Rectum | AC | 2 | 3.7 |
| CRC-84 | F | 81 | 3 | Rectum | AC | 2 | 8.4 |
| CRC-85 | F | 73 | 3 | S-colon | AC | 2 | 1.7 |
| CRC-86 | M | 54 | 3 | Rectum | AC | 2 | 6.4 |
| CRC-87 | F | 58 | 3 | Rectum | AC | 2 | 21.3 |
| CRC-88 | F | 42 | 3 | Rectum | AC | 2 | 0.7 |
| CRC-89 | F | 50 | 3 | D-colon | AC | 2 | 6.4 |
| CRC-90 | M | 56 | 3 | S-colon | AC | 2 | 7.3 |
| CRC-91 | F | 58 | 3 | S-colon | AC | 3 | 2.1 |
| CRC-92 | F | 70 | 4 | Rectum | AC | 2 | 3.9 |
| CRC-93 | M | 68 | 4 | Rectum | AC | 3 | 6.0 |
| CRC-94 | M | 53 | 4 | Rectum | AC | 2 | 54.7 |
| CRC-95 | F | 63 | 4 | D-colon | AC | 2 | 12.3 |

A : Adenoma / AC : Adenocarcinoma /
ASC : Adenosquamous carcinoma /
C : Carcinoid / MAC : Mucinous adenocarcinoma /
SC : Signet-ring cell carcinoma /

FIG. 3D

| CRC | Sex | Age year | Stage | Location | Cell Type | Different-iation | CEA ng/ml |
|---|---|---|---|---|---|---|---|
| CRC-96 | F | 63 | 4 | A-colon | AC | 2 | 1.4 |
| CRC-97 | M | 63 | 2 | D-colon | AC | 3 | 4.9 |
| CRC-98 | F | 66 | 2 | S-colon | AC | 1 | 4.2 |
| CRC-99 | M | 48 | 2 | Rectum | AC | 2 | 28.4 |
| CRC-100 | M | 68 | 2 | S-colon | AC | 2 | 2.3 |
| CRC-101 | M | 48 | 2 | S-colon | AC | 2 | 4.8 |
| CRC-102 | F | 81 | 2 | S-colon | AC | 2 | 2.4 |
| CRC-103 | M | 56 | 2 | A-colon | AC | 2 | 34.6 |
| CRC-104 | M | 71 | 3 | Rectum | AC | 2 | 16.5 |
| CRC-105 | M | 66 | 3 | S-colon | AC | 2 | 689.8 |
| CRC-106 | M | 65 | 3 | D-colon | AC | 2 | 3.4 |
| CRC-107 | F | 65 | 3 | S-colon | MAC | * | 2.7 |
| CRC-108 | F | 51 | 3 | Rectum | AC | 2 | 1.4 |
| CRC-109 | M | 58 | 3 | S-colon | AC | 1 | 2.8 |
| CRC-110 | F | 48 | 3 | A-colon | AC | 1 | 0.9 |
| CRC-111 | M | 71 | 3 | S-colon | AC | 2 | 6.0 |
| CRC-112 | M | 68 | 3 | A-colon | AC | 2 | 2.7 |
| CRC-113 | F | 54 | 3 | A-colon | AC | 2 | 1.7 |
| CRC-114 | M | 66 | 4 | S-colon | AC | 2 | 6.4 |
| CRC-115 | F | 72 | 4 | A-colon | AC | 2 | 73.4 |
| CRC-116 | F | 69 | 4 | A-colon | AC | 2 | 49.0 |
| CRC-117 | M | 75 | 4 | S-colon | AC | 2 | 16.7 |
| CRC-118 | F | 49 | 3 | S-colon | AC | 2 | 1.0 |
| CRC-119 | F | 63 | 3 | A-colon | AC | 2 | 58.2 |

A : Adenoma / AC : Adenocarcinoma /
ASC : Adenosquamous carcinoma /
C : Carcinoid / MAC : Mucinous adenocarcinoma /
SC : Signet-ring cell carcinoma /

FIG. 3E

| CRC | Sex | Age year | Stage | Location | Cell Type | Different-iation | CEA ng/ml |
|---|---|---|---|---|---|---|---|
| CRC-120 | M | 74 | 3 | A-colon | AC | 3 | 2.8 |
| CRC-121 | F | 54 | 3 | T-colon | AC | 2 | 2.2 |
| CRC-122 | M | 68 | 3 | Rectum | AC | 2 | 22.5 |
| CRC-123 | M | 66 | 3 | Rectum | MAC | * | 1.2 |
| CRC-124 | M | 72 | 4 | Rectum | SC | * | 8.2 |
| CRC-125 | M | 73 | 4 | Rectum | AC | 2 | 52.2 |
| CRC-126 | M | 54 | 4 | A-colon | AC | 1 | 2.0 |
| CRC-127 | F | 54 | 4 | S-colon | AC | 2 | 29.8 |
| CRC-128 | M | 43 | 4 | Rectum | AC | 2 | 36.4 |
| CRC-129 | F | 52 | 4 | A-colon | MAC | * | 9.0 |
| CRC-130 | M | 48 | 4 | S-colon | AC | 2 | 15.9 |
| CRC-131 | M | 62 | 4 | Rectum | AC | 2 | 6.3 |
| CRC-132 | M | 77 | 1 | D-colon | AC | 1 | 6.4 |
| CRC-133 | M | 78 | 1 | Rectum | AC | 1 | 2.7 |

A : Adenoma / AC : Adenocarcinoma /
ASC : Adenosquamous carcinoma /
C : Carcinoid / MAC : Mucinous adenocarcinoma /
SC : Signet-ring cell carcinoma /

FIG. 3F

| Control | Sex | Age year | CEA ng/ml | Control | Sex | Age year | CEA ng/ml |
|---|---|---|---|---|---|---|---|
| N-1 | M | 39 | 1.3 | N-29 | M | 50 | 1.9 |
| N-2 | F | 70 | 1.2 | N-30 | M | 46 | 1.5 |
| N-3 | M | 66 | 1.3 | N-31 | M | 51 | 4.0 |
| N-4 | M | 53 | 0.8 | N-32 | F | 68 | 1.8 |
| N-5 | F | 69 | 1.0 | N-33 | F | 68 | 1.4 |
| N-6 | F | 68 | 1.8 | N-34 | M | 64 | 1.7 |
| N-7 | M | 35 | 1.7 | N-35 | M | 30 | 0.7 |
| N-8 | M | 62 | 3.7 | N-36 | F | 52 | 2.1 |
| N-9 | M | 62 | 1.1 | N-37 | F | 59 | 1.2 |
| N-10 | M | 48 | 5.3 | N-38 | M | 53 | 1.6 |
| N-11 | M | 48 | 1.8 | N-39 | F | 69 | 1.2 |
| N-12 | M | 66 | 1.6 | N-40 | F | 68 | 1.0 |
| N-13 | M | 66 | 1.4 | N-41 | F | 65 | 3.1 |
| N-14 | M | 66 | 4.2 | N-42 | M | 31 | 1.2 |
| N-15 | M | 54 | 1.4 | N-43 | F | 59 | 0.7 |
| N-16 | M | 54 | 1.0 | N-44 | M | 43 | 1.4 |
| N-17 | M | 62 | 2.0 | N-45 | M | 66 | 2.3 |
| N-18 | F | 45 | 0.7 | N-46 | M | 48 | 4.2 |
| N-19 | M | 39 | 3.2 | N-47 | F | 41 | 2.1 |
| N-20 | M | 67 | 1.8 | N-48 | F | 65 | 3.8 |
| N-21 | M | 63 | 5.5 | N-49 | F | 67 | 1.5 |
| N-22 | M | 48 | 2.8 | N-50 | F | 45 | 0.6 |
| N-23 | M | 66 | 3.2 | N-51 | M | 30 | 1.0 |
| N-24 | M | 55 | 5.0 | N-52 | M | 55 | 1.2 |
| N-25 | M | 55 | 1.0 | N-53 | M | 54 | 2.1 |
| N-26 | M | 62 | 7.0 | N-54 | M | 69 | 2.8 |
| N-27 | F | 57 | 1.2 | N-55 | M | 53 | 1.8 |
| N-28 | M | 61 | 0.9 | N-56 | F | 47 | 1.7 |

FIG. 4A

| Control | Sex | Age year | CEA ng/ml | Control | Sex | Age year | CEA ng/ml |
|---|---|---|---|---|---|---|---|
| N-57 | M | 31 | 1.7 | N-85 | F | 50 | 1.2 |
| N-58 | M | 53 | 3.2 | N-86 | F | 49 | 2.1 |
| N-59 | F | 49 | 1.4 | N-87 | F | 38 | 0.6 |
| N-60 | M | 62 | 1.7 | N-88 | F | 59 | 1.6 |
| N-61 | M | 31 | 2.3 | N-89 | F | 51 | 1.0 |
| N-62 | M | 40 | 0.8 | N-90 | F | 41 | 1.8 |
| N-63 | F | 49 | 1.4 | N-91 | F | 48 | 1.2 |
| N-64 | F | 33 | 1.7 | N-92 | F | 39 | 0.5 |
| N-65 | M | 51 | 3.4 | N-93 | F | 51 | 1.1 |
| N-66 | M | 52 | 2.0 | N-94 | F | 44 | 1.5 |
| N-67 | F | 66 | 1.3 | N-95 | F | 38 | 1.5 |
| N-68 | M | 56 | 1.9 | N-96 | F | 48 | 1.9 |
| N-69 | F | 65 | 1.4 | N-97 | F | 70 | 4.8 |
| N-70 | M | 50 | 1.4 | N-98 | F | 54 | 2.8 |
| N-71 | M | 54 | 1.3 | N-99 | F | 38 | 2.8 |
| N-72 | M | 68 | 1.6 | N-100 | F | 50 | 1.1 |
| N-73 | M | 59 | 2.5 | N-101 | F | 54 | 1.8 |
| N-74 | F | 51 | 2.1 | N-102 | M | 49 | 1.2 |
| N-75 | F | 39 | 0.8 | N-103 | F | 38 | 0.9 |
| N-76 | F | 40 | 1.5 | N-104 | F | 44 | - |
| N-77 | F | 50 | 1.9 | N-105 | M | 52 | - |
| N-78 | F | 64 | 2.9 | N-106 | F | 45 | - |
| N-79 | F | 52 | 1.9 | N-107 | F | 54 | - |
| N-80 | F | 37 | 2.1 | N-108 | F | 51 | 3.1 |
| N-81 | F | 49 | 2.6 | N-109 | M | 54 | 6.4 |
| N-82 | F | 48 | 1.5 | N-110 | M | 46 | 1.1 |
| N-83 | F | 30 | <0.5 | N-111 | M | 47 | 1.8 |
| N-84 | F | 56 | 1.4 | N-112 | M | 49 | 1.7 |

FIG. 4B

| Control | Sex | Age year | CEA ng/ml | Control | Sex | Age year | CEA ng/ml |
|---|---|---|---|---|---|---|---|
| N-113 | F | 55 | <0.5 | N-134 | F | 44 | - |
| N-114 | M | 36 | 0.7 | N-135 | F | 46 | - |
| N-115 | M | 59 | 0.8 | N-136 | M | 58 | - |
| N-116 | M | 46 | 3.7 | N-137 | M | 45 | 4.3 |
| N-117 | F | 46 | <0.5 | N-138 | M | 61 | 1.4 |
| N-118 | F | 50 | 0.9 | N-139 | M | 42 | 2.7 |
| N-119 | M | 58 | - | N-140 | M | 48 | 3.0 |
| N-120 | M | 34 | 1.7 | N-141 | M | 53 | 1.9 |
| N-121 | M | 53 | 2.9 | N-142 | F | 54 | 2.3 |
| N-122 | M | 45 | 3.7 | N-143 | F | 39 | 1.3 |
| N-123 | M | 47 | 4.5 | N-144 | F | 55 | 1.3 |
| N-124 | F | 34 | 0.6 | N-145 | M | 53 | - |
| N-125 | F | 58 | 1.5 | N-146 | F | 46 | - |
| N-126 | F | 54 | - | N-147 | F | 45 | - |
| N-127 | M | 35 | 1.8 | N-148 | F | 63 | - |
| N-128 | M | 49 | 1.4 | N-149 | F | 51 | - |
| N-129 | M | 48 | 3.2 | N-150 | M | 51 | - |
| N-130 | F | 34 | <0.5 | N-151 | F | 52 | - |
| N-131 | M | 45 | 4.4 | N-152 | F | 52 | - |
| N-132 | F | 45 | 0.8 | N-153 | F | 70 | - |
| N-133 | M | 52 | - | - ; CEA not measured | | | |

FIG. 4C

| CRC | Sex | Age year | Stage | Location | Cell Type | Different -iation | CEA ng/ml |
|---|---|---|---|---|---|---|---|
| CRC-1 | F | 51 | 2 | Rectum | AC | 2 | 6.7 |
| CRC-2 | M | 71 | 1 | Rectum | AC | 2 | 9.8 |
| CRC-3 | F | 47 | 1 | Rectum | AC | 2 | 3.9 |
| CRC-4 | F | 50 | 4 | Rectum | AC | 2 | 62.0 |
| CRC-5 | M | 79 | 2 | S-colon | AC | 1 | 6.2 |
| CRC-6 | F | 54 | 1 | Rectum | AC | 1 | 1.6 |
| CRC-7 | F | 52 | 3 | S-colon | AC | 2 | 22.1 |
| CRC-8 | M | 61 | 3 | Rectum | AC | 1 | 128.1 |
| CRC-9 | F | 47 | 3 | S-colon | AC | 2 | 1.2 |
| CRC-10 | M | 73 | 1 | S-colon | AC | 1 | 7.1 |
| CRC-11 | F | 74 | 1 | S-colon | AC | 1 | 2.3 |
| CRC-12 | M | 71 | 3 | A-colon | AC | 2 | 8.2 |
| CRC-13 | F | 71 | 1 | S-colon | AC | 2 | 2.5 |
| CRC-14 | M | 57 | 4 | Rectum | AC | 2 | 6.4 |
| CRC-15 | M | 57 | 4 | S-colon | AC | 3 | 41.7 |
| CRC-16 | M | 52 | 3 | S-colon | AC | 2 | 4.1 |
| CRC-17 | F | 64 | 3 | S-colon | AC | 3 | 6.8 |
| CRC-18 | M | 48 | 4 | A-colon | AC | 2 | 59.4 |
| CRC-19 | F | 51 | 3 | S-colon | AC | 2 | 1.2 |
| CRC-20 | M | 67 | 4 | Rectum | AC | 2 | 16.2 |
| CRC-21 | M | 71 | 1 | Rectum | AC | 2 | 83.7 |

FIG. 5A

| CRC | Sex | Age year | Stage | Location | Cell Type | Different -iation | CEA ng/ml |
|---|---|---|---|---|---|---|---|
| CRC-22 | M | 59 | 1 | S-colon | AC | 1 | 3.0 |
| CRC-23 | F | 66 | 4 | S-colon | AC | 2 | 18.5 |
| CRC-24 | F | 78 | 4 | A-colon | AC | 2 | 12.6 |
| CRC-25 | M | 55 | 3 | A-colon | AC | 2 | 1.2 |
| CRC-26 | M | 62 | 3 | Rectum | AC | 2 | 2.5 |
| CRC-27 | M | 38 | 3 | Rectum | AC | 2 | 6.1 |
| CRC-28 | F | 65 | 3 | D-colon | AC | 3 | 3.5 |
| CRC-29 | M | 49 | 3 | S-colon, T-colon | AC | 2 | 3.8 |
| CRC-30 | F | 59 | 2 | A-colon | AC | 2 | 1 |
| CRC-31 | M | 62 | 2 | S-colon | AC | 1 | * |
| CRC-32 | F | 62 | 1 | Rectum | AC | 2 | 1.4 |
| CRC-33 | F | 54 | 4 | S-colon | AC | 3 | 27.9 |
| CRC-34 | M | 70 | Tis | S-colon | AC | 1 | 2 |
| CRC-35 | M | 66 | 3 | S-colon | AC | 2 | 10.7 |
| CRC-36 | M | 35 | 3 | Rectum | C | - | 2.8 |
| CRC-37 | M | 84 | 2 | S-colon | AC | 1 | 11.3 |
| CRC-38 | F | 54 | 3 | S-colon | AC | 2 | 8.8 |
| CRC-39 | M | 68 | 2 | Rectum | AC | 2 | 5.8 |
| CRC-40 | M | 54 | 2 | A-colon | AC | 1 | 1.1 |
| CRC-41 | M | 62 | 3 | S-colon | AC | 2 | 10.8 |
| CRC-42 | M | 66 | 1 | S-colon | AC | 2 | 2.6 |
| CRC-43 | F | 60 | 3 | S-colon, A-colon | AC | 2 | 28.5 |
| CRC-44 | F | 51 | 2 | D-colon | AC | 2 | 5.9 |
| CRC-45 | F | 73 | 3 | Rectum | AC | 2 | 3.7 |
| CRC-46 | F | 54 | 3 | D-colon | AC | 2 | 1122.2 |
| CRC-47 | M | 64 | 1 | Rectum | AC | 2 | 2.5 |

FIG. 5B

| CRC | Sex | Age year | Stage | Location | Cell Type | Different -iation | CEA ng/ml |
|---|---|---|---|---|---|---|---|
| CRC-48 | F | 69 | 2 | S-colon, A-colon | AC | 2 | 5.1 |
| CRC-49 | M | 43 | 1 | Rectum | AC | 2 | 1.0 |
| CRC-50 | M | 39 | 2 | S-colon | A | 1 | 2.9 |
| CRC-51 | M | 58 | Adenoma | A-colon | AC | - | 2 |
| CRC-52 | M | 49 | 1 | Rectum | AC | 2 | 6.6 |
| CRC-53 | F | 60 | 3 | A-colon | AC | 2 | 30.4 |
| CRC-54 | M | 69 | 4 | A-colon | AC | 2 | 33.5 |
| CRC-55 | M | 43 | 3 | A-colon | MAC | - | 77.6 |
| CRC-56 | F | 69 | 3 | Rectum | AC | 2 | 1.0 |
| CRC-57 | M | 72 | 3 | A-colon | AC | 2 | 2.4 |
| CRC-58 | F | 58 | 1 | A-colon | AC | 2 | 1.0 |
| CRC-59 | M | 54 | 2 | Rectum | AC | 2 | 4.6 |
| CRC-60 | M | 58 | 2 | S-colon | AC | 1 | 2.9 |
| CRC-61 | F | 52 | 3 | S-colon | AC | 2 | 9.2 |
| CRC-62 | M | 52 | 3 | S-colon | AC | 2 | 3.2 |
| CRC-63 | M | 78 | 4 | Rectum | AC | 2 | 4.1 |
| CRC-64 | F | 55 | 3 | Rectum | AC | 2 | 0.9 |
| CRC-65 | M | 65 | 2 | S-colon | AC | 1 | 1.7 |
| CRC-66 | F | 46 | 1 | S-colon | AC | 2 | 1.4 |
| CRC-67 | M | 77 | 3 | S-colon | AC | 2 | 2.5 |
| CRC-68 | M | 52 | Tis | Rectum | AC | 1 | 0.6 |
| CRC-69 | F | 52 | 2 | S-colon | AC | 2 | <0.5 |
| CRC-70 | F | 47 | 3 | S-colon | AC | 2 | 1.5 |
| CRC-71 | M | 48 | 3 | S-colon | AC | 2 | 1.7 |
| CRC-72 | F | 76 | 2 | S-colon | AC | 2 | 2.2 |
| CRC-73 | M | 51 | 2 | S-colon | ASC | * | 8.6 |
| CRC-74 | M | 61 | 1 | Rectum | AC | 2 | 1.4 |

FIG. 5C

| CRC | Sex | Age year | Stage | Location | Cell Type | Different-iation | CEA ng/ml |
|---|---|---|---|---|---|---|---|
| CRC-75 | M | 56 | 2 | Rectum | AC | 2 | 3 |
| CRC-76 | F | 70 | 3 | S-colon | MAC | - | 36.0 |
| CRC-77 | M | 64 | 3 | A-colon | AC | 1 | 2.2 |
| CRC-78 | F | 54 | 3 | Rectum | AC | 2 | 5.5 |
| CRC-79 | F | 77 | 2 | Rectum | AC | 2 | 6.2 |
| CRC-80 | M | 53 | 3 | Rectum | AC | 2 | 1.4 |
| CRC-81 | M | 43 | 1 | Rectum | AC | 2 | 0.5 |
| CRC-82 | M | 81 | 3 | A-colon | MAC | - | 10.9 |
| CRC-83 | F | 52 | 3 | A-colon | AC | 2 | 1.2 |
| CRC-84 | F | 71 | 3 | A-colon | AC | 2 | 2.8 |
| CRC-85 | M | 84 | 3 | Rectum | AC | 2 | 15.0 |
| CRC-86 | F | 33 | 3 | D-colon | AC | 2 | 4.7 |
| CRC-87 | F | 68 | 3 | Rectum | AC | 2 | 3.3 |
| CRC-88 | M | 69 | 3 | Rectum | AC | 2 | 3.5 |
| CRC-89 | F | 61 | 3 | A-colon | AC | 2 | 2.8 |
| CRC-90 | M | 44 | 2 | T-colon | AC | 1 | 1.8 |
| CRC-91 | F | 52 | 1 | S-colon | AC | 1 | 2.2 |
| CRC-92 | F | 82 | 2 | A-colon | AC | 2 | 2.8 |
| CRC-93 | M | 38 | 1 | Rectum | AC | 2 | 2.1 |
| CRC-94 | M | 73 | 3 | Rectum | AC | 2 | 11.1 |
| CRC-95 | M | 64 | 3 | D-colon | AC | 2 | 8.2 |
| CRC-96 | M | 48 | Tis | S-colon | AC | 1 | 2.6 |

FIG. 5D

| CRC | Sex | Age year | Stage | Location | Cell Type | Different-iation | CEA ng/ml |
|---|---|---|---|---|---|---|---|
| CRC-97 | M | 67 | 2 | A-colon | AC | 2 | 20.1 |
| CRC-98 | M | 72 | 2 | A-colon | AC | 2 | 3.4 |
| CRC-99 | M | 59 | 2 | S-colon | AC | 2 | 2.1 |
| CRC-100 | M | 53 | 1 | Rectum | AC | 1 | 3.5 |
| CRC-101 | M | 74 | 2 | Rectum | AC | 2 | 7.9 |
| CRC-102 | F | 59 | 3 | Rectum | AC | 2 | 1.4 |
| CRC-103 | M | 56 | 1 | Rectum | AC | 2 | 2.6 |
| CRC-104 | M | 69 | 2 | Rectum | AC | 2 | 14.0 |
| CRC-105 | M | 58 | 2 | Rectum | AC | 2 | 10.2 |
| CRC-106 | F | 75 | 1 | Rectum | AC | 2 | 2.4 |
| CRC-107 | M | 47 | 2 | Rectum | AC | 2 | 3.2 |
| CRC-108 | F | 68 | 2 | Rectum | AC | 2 | 0.7 |
| CRC-109 | M | 52 | 3 | Rectum | AC | 2 | 2.9 |
| CRC-110 | M | 68 | 1 | Rectum | AC | 2 | 7.0 |
| CRC-111 | M | 51 | 2 | Rectum | AC | 1 | 1.4 |
| CRC-112 | M | 66 | 0 | Rectum | AC | 2 | 1.2 |
| CRC-113 | M | 74 | 0 | Rectum | AC | 2 | 4.5 |
| CRC-114 | M | 43 | 2 | Rectum | AC | 2 | 12.3 |
| CRC-115 | M | 68 | 3 | Rectum | AC | 2 | 2.5 |
| CRC-116 | M | 68 | 3 | Rectum | AC | 1 | 19.4 |
| CRC-117 | F | 56 | 1 | Rectum | AC | 2 | 2.3 |
| CRC-118 | M | 63 | 0 | Rectum | AC | 1 | 1.3 |
| CRC-119 | M | 65 | 2 | Rectum | AC | 1 | 2.1 |
| CRC-120 | M | 60 | 2 | Rectum | AC | 2 | 4.6 |
| CRC-121 | M | 51 | 2 | Rectum | AC | 2 | 1.3 |
| CRC-122 | M | 44 | 0 | Rectum | AC | 2 | 2.2 |
| CRC-123 | M | 61 | 2 | Rectum | AC | 2 | 2.0 |
| CRC-124 | M | 57 | 3 | Rectum | AC | 2 | 2.2 |
| CRC-125 | M | 70 | 2 | Rectum | AC | 2 | 1.3 |

FIG. 5E

| CRC | Sex | Age year | Stage | Location | Cell Type | Differentiation | CEA ng/ml |
|---|---|---|---|---|---|---|---|
| CRC-126 | M | 55 | 2 | Rectum | AC | 2 | 22.0 |
| CRC-127 | M | 62 | 2 | Rectum | AC | 2 | 6.1 |
| CRC-128 | M | 64 | 3 | Rectum | AC | 2 | 4.8 |
| CRC-129 | M | 62 | 4 | Rectum | AC | 2 | 25.3 |
| CRC-130 | M | 51 | 3 | Rectum | AC | 2 | 149.3 |
| CRC-131 | F | 45 | 2 | Rectum | AC | 2 | 2.7 |
| CRC-132 | F | 49 | 2 | Rectum | AC | 2 | 2.1 |
| CRC-133 | F | 45 | 0 | Rectum | AC | 2 | 0.9 |
| CRC-134 | M | 62 | 3 | Rectum | AC | 2 | 2.4 |
| CRC135 | M | 54 | 0 | Rectum | AC | 2 | 6.9 |
| CRC-136 | M | 45 | 0 | Rectum | AC | 1 | 7.4 |
| CRC-137 | F | 54 | 0 | Rectum | AC | 1 | 3.6 |
| CRC-138 | M | 69 | 2 | Rectum | AC | 2 | 24.0 |
| CRC-139 | M | 51 | 1 | Rectum | AC | 1 | 2.7 |
| CRC-140 | M | 45 | 1 | Rectum | AC | 2 | 3.2 |
| CRC-141 | M | 67 | 1 | Rectum | AC | 2 | 2.9 |
| CRC-142 | M | 60 | 1 | Rectum | AC | 2 | 1.5 |
| CRC-143 | M | 49 | 0 | Rectum | AC | 2 | 0.8 |
| CRC-144 | M | 71 | 1 | Rectum | AC | 2 | 9.8 |

FIG. 5F

| Control | Sex | Age year | CEA ng/ml | Control | Sex | Age year | CEA ng/ml |
|---|---|---|---|---|---|---|---|
| N-1 | M | 64 | 2.4 | N-27 | F | 52 | 1.7 |
| N-2 | M | 53 | 3.3 | N-28 | M | 63 | 1.0 |
| N-3 | M | 63 | 0.9 | N-29 | F | 60 | 1.8 |
| N-4 | M | 57 | 1.5 | N-30 | F | 58 | 0.7 |
| N-5 | F | 66 | 1.6 | N-31 | M | 65 | 4.1 |
| N-6 | M | 60 | 1.5 | N-32 | M | 52 | 2.2 |
| N-7 | M | 57 | 2.2 | N-33 | F | 58 | 3.1 |
| N-8 | M | 53 | 1.9 | N-34 | M | 65 | 2.8 |
| N-9 | M | 60 | 0.8 | N-35 | M | 66 | 0.8 |
| N-10 | F | 50 | 2.6 | N-36 | M | 69 | 2.1 |
| N-11 | F | 53 | 2.6 | N-37 | F | 54 | 1.6 |
| N-12 | M | 64 | 1.5 | N-38 | M | 50 | 1.9 |
| N-13 | F | 60 | 3.7 | N-39 | F | 60 | 1.1 |
| N-14 | M | 58 | 1.2 | N-40 | F | 55 | 8.8 |
| N-15 | F | 66 | 1.1 | N-41 | M | 62 | 0.9 |
| N-16 | M | 57 | 2.9 | N-42 | F | 51 | 2.0 |
| N-17 | F | 68 | 5.5 | N-43 | M | 65 | 2.3 |
| N-18 | M | 56 | 1.7 | N-44 | M | 52 | 2.4 |
| N-19 | M | 51 | 3.4 | N-45 | F | 64 | 1.7 |
| N-20 | F | 56 | 1.3 | N-46 | M | 57 | 0.8 |
| N-21 | M | 57 | 1.5 | N-47 | F | 54 | <0.5 |
| N-22 | M | 61 | 4.2 | N-48 | F | 59 | 0.8 |
| N-23 | F | 51 | 1.9 | N-49 | F | 65 | 1.6 |
| N-24 | F | 51 | 1.6 | N-50 | F | 68 | 1.6 |
| N-25 | F | 52 | 1.4 | N-51 | F | 51 | 1.7 |
| N-26 | F | 56 | 1.7 | N-52 | F | 62 | 1.3 |

FIG. 6A

| Control | Sex | Age year | CEA ng/ml | Control | Sex | Age year | CEA ng/ml |
|---|---|---|---|---|---|---|---|
| N-53 | M | 54 | 4.2 | N-77 | F | 65 | 1.1 |
| N-54 | F | 63 | 1.6 | N-78 | M | 64 | 1.4 |
| N-55 | F | 60 | 1.9 | N-79 | F | 55 | 4.8 |
| N-56 | F | 68 | 1.4 | N-80 | M | 63 | 2.6 |
| N-57 | F | 62 | 1.9 | N-81 | F | 52 | 4.1 |
| N-58 | F | 68 | 5.6 | N-82 | M | 51 | 4.0 |
| N-59 | M | 63 | 4.5 | N-83 | M | 59 | 2.0 |
| N-60 | M | 50 | 2.1 | N-84 | M | 68 | 4.6 |
| N-61 | F | 53 | 2.3 | N-85 | M | 50 | 5.0 |
| N-62 | M | 60 | 3.3 | N-86 | F | 64 | <0.5 |
| N-63 | M | 64 | 1.8 | N-87 | F | 63 | 2.2 |
| N-64 | M | 63 | 3.4 | N-88 | M | 64 | 1.7 |
| N-65 | F | 63 | 1.1 | N-89 | M | 51 | 2.3 |
| N-66 | M | 53 | 2.0 | N-90 | F | 62 | 1.1 |
| N-67 | F | 51 | 2.0 | N-91 | M | 54 | 2.5 |
| N-68 | M | 57 | 3.3 | N-92 | F | 53 | 0.7 |
| N-69 | M | 61 | 2.8 | N-93 | F | 65 | 3.8 |
| N-70 | F | 68 | 1.4 | N-94 | F | 64 | 1.5 |
| N-71 | F | 52 | 1.5 | N-95 | F | 53 | 1.0 |
| N-72 | M | 60 | 4.6 | N-96 | M | 50 | 1.1 |
| N-73 | M | 55 | 2.2 | N-97 | F | 66 | 1.7 |
| N-74 | M | 55 | 1.8 | N-98 | F | 50 | 1.0 |
| N-75 | M | 56 | 2.2 | N-99 | F | 50 | 1.9 |
| N-76 | F | 63 | 1.8 | N-100 | M | 61 | 1.5 |

FIG. 6B

| CRC No. in Validation Set (Suppl Table 2B) | Regression Grade | CRC No. in Validation Set (Suppl Table 2B) | Regression Grade |
|---|---|---|---|
| CRC-101 | 2 | CRC-123 | 2 |
| CRC-102 | 2 | CRC-124 | 1 |
| CRC-103 | 2 | CRC-125 | 2 |
| CRC-104 | 1 | CRC-126 | 2 |
| CRC-105 | 2 | CRC-127 | 2 |
| CRC-106 | 2 | CRC-128 | 2 |
| CRC-107 | 2 | CRC-129 | 2 |
| CRC-108 | 2 | CRC-130 | 1 |
| CRC-109 | 1 | CRC-131 | 1 |
| CRC-110 | 2 | CRC-132 | 3 |
| CRC-111 | 2 | CRC-133 | 3 |
| CRC-112 | 3 | CRC-134 | 2 |
| CRC-113 | 4 | CRC-135 | 4 |
| CRC-114 | 1 | CRC-136 | 3 |
| CRC-115 | 2 | CRC-137 | 4 |
| CRC-116 | 3 | CRC-138 | 2 |
| CRC-117 | 2 | CRC-139 | 2 |
| CRC-118 | 4 | CRC-140 | 3 |
| CRC-119 | 2 | CRC-141 | 2 |
| CRC-120 | 2 | CRC-142 | 2 |
| CRC-121 | 2 | CRC-143 | 4 |
| CRC-122 | 4 | CRC-144 | 2 |

FIG. 7

METHOD FOR CRYSTALLIZING LOW MASS IONS FOR DIAGNOSING COLORECTAL CANCER AND METHOD FOR DIAGNOSING COLORECTAL CANCER USING SAME

CROSS REFERENCE TO RELATED APPLICATION

This is a National Stage of International Application No. PCT/KR2011/005974, filed 12 Aug. 2011, which claims the benefit of Application No. 10-2010-0078017, filed in Korea on 12 Aug. 2010 and Application No. 10-2010-0100473 filed in Korea on 14 Oct. 2010, the disclosures of which Applications are incorporated by reference herein.

TECHNICAL FIELD

The present invention relates to a method for determining low mass ions for diagnosing colorectal cancer by conducting biostatistical analysis on low mass ions extracted from a biological sample using MALDI-TOF (matrix assisted laser desorption ionization-time of flight) mass spectrometry, and providing information for diagnosing colorectal cancer using the same.

BACKGROUND ART

Cancer is a disease in which functions of normal cells are hindered by indefinite proliferation of cells. Representative examples of cancer include lung cancer, gastric cancer, breast cancer ("BRC"), colorectal cancer ("CRC"), and so on, but cancer can develop virtually any place of the body. While the early stage of cancer diagnosis technology focused on the external changes of biological tissues depending on growth of cancer cells, the recent attempts adopt diagnosis and detection based on biological tissues such as blood, glycol-chain, or DNAs or a trace of biological molecules present on cells. Among these, the most general cancer diagnostic method is done by using tissue samples obtained from biopsy, or imaging technology.

The biopsy has shortcomings including tremendous pain, expensive cost and lengthy time until the diagnosis. If a patient suspected of cancer indeed has cancer, there is a possibility that the cancer spreads during biopsy. Further, for specific sites of a body where biopsy is limited, diagnosing is often not available until suspicious tissues are extracted by surgical operation.

The imaging-based diagnosis basically determines the cancer based on the X-ray image, the nuclear magnetic resonance (NMR) images, or the like, using contrast agent to which disease-targeting substance is attached. The shortcomings of the imaging-based diagnosis include possibility of misdiagnosis depending on expertise of clinician or personnel who reads the data, and high dependency on the precision of the image-acquisition devices. Furthermore, even the device with the upmost precision is not able to detect a tumor under several mm in size, which means that early detection is unlikely. Further, in the process of image acquisition, as a patient is exposed to high energy electromagnetic wave which itself can induce mutation of genes, there is possibility that another disease may be induced and the number of diagnosis by imaging is limited.

Presence and absence of disease in gastric system is generally determined by observation by naked eyes with the use of endoscope. The process is painful and even when abnormality is observed during this examination, biopsy is still required to accurately determine whether the cancer is malignant/benign tumor, polypus, etc.

CRC is the third most commonly diagnosed cancer in the world and the cure thereof hugely depends on the stages of cancer development. That is, CRC is highly curable when detected at an early stage by screening. While early detection is very important, symptoms of this cancer are not palpable until the patient perceives the possibility from changed color of excretion due to presence of blood therein. Generally, a patient or a person suspected of CRC first goes thorough endoscopic examination of large intestines and then necessarily takes biopsy to accurately determine specific disease. That is, for CRC, early detection is critical, but since endoscopic examination of large intestines and biopsy take tremendous time and cost and also are inconvenient and painful, a diagnosis method is necessary, which can considerably reduce the number of subjects of the endoscopic examination and biopsy which can be unnecessary.

Accordingly, by providing CRC screening at an early stage based on new molecular approach, patients will be benefited. The genomics, proteomics and molecular pathology have provided various biomarker candidates with clinical potentials. It will be possible to improve treatment effect by actively utilizing the biomarker candidates in the customized treatment of cancers according to stages and patients, and therefore, many researches are necessary to apply the above in the actual clinical treatment.

The recent CRC screening test includes determination of gross abnormality by endoscopic examination of large intestines, or fecal occult blood test (FOBT) which detects blood in feces. The endoscopic examination of large intestines has been utilized as a standard way of examination in the CRC screening, but due to invasiveness thereof, patients who can receive the examination are limited. Accordingly, many attempts have been focused on the examination of feces, for advantages such as noninvasiveness, no need for colonic irrigation, and transferability of the sample. The fecal marker may include feces oozing, excreted or exfoliated from the tumor. For example, hemoglobin in traditional FOBT was perceived as the oozing type of the marker in the large scale screening program. However, the markers known so far, including the above, have not met the satisfaction.

Meanwhile, it is possible to extract spectra of mass ions within blood using the matrix-assisted laser desorption/ionization-time of flight (MALDI-TOF) mass spectrometer. The mass spectrometry, generally used in the researches on proteins, mainly categorizes 800 to 2500 m/s mass range as the target of analysis, because the specific range corresponds to the mass value region of peptide when the protein is dissociated by trypsin. It is also possible to extract the mass spectra of los-mass ions by using MALDI-TOF mass spectrometer. However, for the low mass region below approximately 800 m/z where the matrix mass ions coexist, research has not been active on this particular region.

The extracted low mass ion mass spectra can be analyzed by the conventional software, MarkerView™ (version 1.2). The inventors of the present invention analyzed mass spectra of the low mass ions extracted from the serums of CRC patient group and normal group (control, CONT) using MarkerView™ in a manner that will be explained in detail below with reference to FIG. 1.

The low mass ion mass spectra in T2D file format was imported with MarkerView™ from the set ($A_1$) of samples of serums collected from 133 CRC patients and 153 normal controls (11). The condition for import was:

TABLE 1

| | |
|---|---|
| Mass tolerance | 100 ppm |
| Minimum required response | 10.0 |
| Maximum number of peaks | 10000 |

The imported peak intensities were then normalized (A12). MarkerView™ has a plurality of normalization methods, and among these, "Normalization Using Total Area Sums" was employed for the normalization. According to the method, partial sums of the intensities of the respective samples were obtained and mean is obtained, and then each peak intensity was multiplied by a scaling factor so that the sums of the respective samples were in agreement with the mean values. As a result, the partial sums of the intensities of the respective samples became identical after the normalization.

Next, the normalized peak intensities were Pareto-scaled (A13). That is, the peak intensities were Pareto-scaled by subtracting the mean values of the respective mass ions from the respective normalized peak intensities, and dividing the same by the square root of the standard deviation.

Next, with respect to the Pareto-scaled peak intensities, discriminant scores (DS) were computed by performing the principal component analysis-based linear discriminant analysis (PCA-DA) (A14). The PCA-DA was performed by two stages, to obtain factor loadings, which are the weighting factors of the respective mass ions, and the Pareto-scaled intensities were multiplied by the factor loadings. The resultant values were summed, to compute the discriminant scores of the respective samples. The import condition of Table 103 includes maximum 10,000 peaks with sufficient samples imported, so that there were 10,000 factor loadings computed, and one DS was computed by summing 10,000 terms.

Next, it was determined whether the computed DS was positive number or not (A15), and if so, determined positive (A16), and if not, determined negative (A17). In other words, when implemented on CRC, the positive number was interpreted as CRC patient group, while negative number was interpreted as normal control group.

FIG. 2 illustrates distribution of DS which were computed by the method of FIG. 1 with respect to the set consisting of 133 clinically CRC-diagnosed patients and 153 non-cancer subjects. Confusion matrix may summarize and represent the determination results according to the determinant scores. As used herein, the confusion matrix is defined as 3×3 on the right, lower part of Table 2.

TABLE 2

| | | Result of Clinical Study | | |
|---|---|---|---|---|
| | | Patient | Non-patient | |
| PCA-DA Prediction Result | Patient | True positive (TP) | False positive (FP) | Positive Predictive Value (PPV) |
| | Non-patient | False negative (FN) | True negative (TN) | Negative Predictive Value (NPV) |
| | | Sensitivity | Specificity | |

That is, while the confusion matrix basically consists of the number of true positive (IP), false positive (FP), false negative (FN), true negative (TN) instances, sensitivity, specificity, positive predictive value (PPV) and negative predictive value (NPV) are also added for convenience of analysis. Accordingly, the determination results according to the determinant scores of FIG. 2 can be summarized by the confusion matrix as follows:

TABLE 3

| 131 | 2 | 98.5% |
|---|---|---|
| 2 | 151 | 98.7% |
| 98.5% | 98.7% | |

Referring to FIG. 2 and Table 3, excellent discrimination result was obtained with all of the sensitivity, specificity, positive predictive value (PPV) and negative predictive value (NPV) exceeding 98% by the conventional PCA-DA of the MarkerView™.

However, the robustness of the formula must be verified for clinical use. That is, even the mass spectra that were additionally measured by a number of times with respect to the dataset that was measured once and constituted discriminant formula, are required to maintain good discrimination results, and the discrimination result based on the same discriminant also has to be sound with respect to new CRC patient groups and non-cancer subjects that were not taken into consideration in the designing of the discriminant. The process of repeatedly measuring mass spectra may include the process of freezing and thawing serums and mixing the serum newly with methanol/chloroform to obtain extract. These processes are considered the disturbances in the statistic analysis with respect to the mass spectra, and clinical implementation is only possible when the discriminant is least influenced by the disturbances.

To sum up, although the conventional PCA-DA explained above with reference to FIGS. 1 and 2 and Tables 1, 2, 3 sometimes exhibit good discrimination result when applied individually to the set of specific samples, i.e., to individual training set, the discrimination result was unsatisfactory when applied with respect to the validation set (Table 7). It appears that the discriminant exhibiting very good discrimination result with respect to the training set, is not so robust because the 10,000 mass ions constituting the discriminant include a considerable amount of mass ions which may be at least unnecessary for the discrimination between patients and non-patient subjects and although not entirely problematic in the discrimination of training set, which can potentially cause confusion in the discrimination result in the discrimination of the validation set. Accordingly, a process is necessary, which exclusively locates mass ions that are absolutely necessary to obtain good and robust discrimination result, by actively removing mass ions which are at least unnecessary or which can potentially confuse discrimination result.

DISCLOSURE

Technical Problem

The invention proposes a discriminant which may provide robust discrimination result to colorectal (CRC) patient and non-patient samples. That is, the invention proposes a discriminant of 80% or higher sensitivity, specificity, positive predictive value and negative predictive value, with respect to mass spectra obtained by several additional repetitive measures on sets of CRC patients and non-patients and to mass spectra obtained by several repetitive measures on new sets of CRC patients and non-patients, and proposes a method for determining low mass ions constructing the same.

To achieve the above-mentioned objects, the present invention provides a method for determining low mass ions for diagnosing CRC.

Means to Solve the Problem

In one embodiment, a method for determining low mass ion for diagnosing colorectal cancer (CRC) is provided, which may include steps of: (a) aligning peak intensities of low mass ions measured from biological samples of a plurality of cases and acquiring the same, (b) performing a biostatistical analysis on the acquired peak intensities, (c) selecting predetermined cases from among the plurality of cases based on a result of the biostatistical analysis, and (d) re-performing the biostatistical analysis on the predetermined training set cases and finally selecting mass value of the low mass ions for diagnosing CRC.

The step (d) may include a step (d1) of primarily selecting peaks of the respective cases from among the peaks, in which the primarily selected peaks meet a condition that an absolute value of a product of the peak intensities multiplied by factor loadings of the respective peaks exceeds $T_1$. $T_1$ may preferably be 0.1.

The step (d) may include a step (d2) of secondarily selecting peaks from the primarily selected peaks for the respective cases, in which the secondarily selected peaks are commonly present in the cases which are $T_2$ or greater percent of the training set cases. $T_2$ may preferably be 50.

The step (d) may include steps of (d1) of primarily selecting peaks of the respective cases from among the peaks, in which the primarily selected peaks meet a condition that an absolute value of a product of the peak intensities multiplied by factor loadings of the respective peaks exceeds $T_1$ and (d2) of secondarily selecting peaks from the primarily selected peaks for the respective cases, in which the secondarily selected peaks are commonly present in the cases which are $T_2$ or greater percent of the training set cases. After the step (d2), discriminant score (DS) may be calculated only with the peaks selected at the step (d2) so that sensitivity and specificity are calculated according to the calculated DS, and if the calculated sensitivity is less than $N_3$ or if the calculated specificity is less than $N_4$, the $T_1$ and $T_2$ may be changed so that the steps (d1) and (d2) reiterate. The $N_3$ and $N_4$ may preferably be 0.9, respectively.

The step (d) may additionally include a step (d3) of selecting predetermined peaks from among the peaks selected at the step (d2) to calculate DS for validation set cases, calculating sensitivity and specificity according to the calculated DS, and if the calculated sensitivity is less than $N_5$ or if the calculated specificity is less than $N_6$, re-selecting new peaks that are different from the predetermined peaks and reiterating a process of improving discrimination performance with respect to validation set cases and finally selecting mass value of the low mass ions for diagnosing CRC. The $N_5$ and $N_6$ may be 0.8, respectively.

The mass value of the low mass ions may preferably be any one selected from a group consisting of: 86.1, 104.1, 105.1, 137.0, 169.0, 181.1, 316.2, 342.2, 344.3, 368.3, 370.3, 468.3, 482.3, 495.3, 510.3, 519.3, 525.3 and 1465.6 m/z.

The number of the low mass ions for diagnosing CRC may be 19, and the mass value of the low mass ions for diagnosing CRC may preferably be 86.1, 104.1, 105.1, 137.0, 169.0, 181.1, 316.2, 342.2, 344.3, 368.3, 370.3, 468.3, 482.3, 495.3, 510.3, 519.3, 525.3 and 1465.6 m/z.

The low mass ions for diagnosing CRC may preferably include low mass ions of fibrinogen or fibrinogen alpha chain. Further, the low mass ions for diagnosing CRC may preferably include low mass ions of phosphoenolpyruvate (PEP).

The step (c) may include steps of (c1) calculating sensitivity and specificity according to the calculated DS, (c2) excluding false positive or false negative cases from the plurality of cases, if the sensitivity is less than $N_1$ or if the specificity is less than $N_2$, and reiterating the steps (a) to (b), and (c3) selecting the cases as the predetermined training set cases if the sensitivity is equal to or greater than $N_1$ and if the specificity is equal to or greater than $N_2$. The $N_1$ and the $N_2$ may preferably be 1, respectively.

The step (a) may preferably include a step (a1) of aligning low mass ion mass spectra acquired from the biological samples of the plurality of cases and importing.

The step (b) may preferably include steps of (b1) normalizing the imported peak intensities, (b2) scaling the normalized peak intensities, and (b3) calculating the DS by performing a biostatistical analysis on the scaled peak intensities. The scaling may preferably be a Pareto scaling. The biostatsitical analysis may preferably be a principal component analysis-based linear discriminant analysis (PCA-DA).

To solve the objects discussed above, the present invention provides a method for providing information for diagnosing colorectal cancer (CRC), using the low mass ions for diagnosing CRC determined as explained above.

To be specific, the method may include steps of: (A) aligning peak intensities of low mass ions measured from samples for discrimination and acquiring the same, (B) normalizing the acquired peak intensities and scaling the same, (C) calculating a discriminant score (DS) with the normalized and scaled peak intensities of the low mass ions for diagnosing CRC and factor loadings of the respective peaks, and (D) determining presence or absence of CRC depending on the calculated DS.

The step (A) may preferably include a step (A1) of aligning the low mass ion mass spectra of the samples for discrimination to the training set and importing.

The step (B) may preferably include steps of (B1) normalizing the imported peak intensities, and (B2) scaling the normalized peak intensities. The scaling may preferably be a Pareto scaling.

The step (C) may preferably include a step (C1) of calculating the discriminant score (DS) with the normalized and scaled peak intensities of the low mass ions for diagnosing CRC with respect to the samples for discrimination, and with factor loadings of the respective peaks acquired by principal component analysis-based linear discriminant analysis (PCA-DA) with respect to training set.

The step (D) may preferably include a step (D1) of determining positive if the DS is equal to or greater than S, and determining negative if the DS is less than S. The S may preferably be 0 or 5.5.

The step (D) may preferably include a step (D1') of determining positive if the DS is equal to or greater than $S_1$, determining negative if the DS is less than $S_2$, and determining on-hold if the DS is greater than $S_2$ and less than $S_1$. The $S_1$ may preferably be 10 and the $S_2$ may preferably be −10.

The step (D) may additionally include a step (D2') of re-determining the subjects determined to be on-hold, by conducting stratified analysis.

Further, the present invention provides a calculating apparatus for performing the method for determining low mass ions for diagnosing colorectal cancer (CRC) as explained above, or performing a method for generating information for diagnosing CRC as explained above.

Further, because the above-explained method for determining low mass ions for diagnosing CRC can be easily converted to a method for determining low mass ions for predicting progress of CRC by changing the CRC patient and non-patient sets to, for example, a patient set in initial stage of CRC and a patient set in late stage of CRC, a method for generating information for predicting progress of CRC in individual patients may be provided, which may use low mass ions for predicting progress of CRC.

Further, because the above-explained method for determining low mass ions for diagnosing CRC can be easily converted to a method for determining low mass ions for predicting treatment reactivity by changing the CRC patient and non-patient sets to, for example, a patient set responsive to treatment and a patient set non-responsive to treatment, a method for generating information for predicting reactivity to a specific treatment of individual patients may be provided, which may use low mass ions for predicting progress of CRC.

Advantageous Effects

A method for determining low mass ions for diagnosing CRC and a CRC diagnosing method using the same according to the present invention provide advantages including low analysis cost, short analysis time and availability of large-scale analysis. For example, it is possible to directly determine presence or absence of CRC by measuring low mass ion mass spectra of the blood, extracting peak intensities corresponding to the mass of the low mass ions for diagnosing CRC and then conducting simple calculations.

Further, in addition to the superior and robust discrimination performance, all the sensitivity, specificity, positive predictive value and negative predictive value exceeded 80% in the discrimination of not only the raining set, but also the validation sets.

Further, the method for determining low mass ions for diagnosing CRC can be easily converted to a method for monitoring progress of CRC in individual patients or predicting effect of a specific treatment on the individual patients, by changing the CRC patient and non-patient groups to, for example, CRC initial stage patient and late stage patient sets or to patient set responsive to treatment and patient set non-responsive to treatment.

Further, compared to the discrimination performance of the general conventional FOBT which studies feces as the analyte to discriminate CRC, the method for determining low mass ions for diagnosing CRC according to the present invention using blood as analyte can be conducted along with the other inspections so that more convenient and rapid CRC diagnosis than the conventional technology is enabled. It was confirmed that use of the low mass ions for diagnosing CRC provided discrimination performance comparable to that of the conventional FOBT, by adjusting the cutoff value S, which is the discriminant score to provide discrimination, from 0 to 5.5.

BRIEF DESCRIPTION OF DRAWINGS

FIG. 1 is a flowchart provided to explain a process of determining CRC using low mass ion mass spectra according to a conventional art.

FIG. 2 shows the result of discriminating basic set consisting of 133 CRC patients and 153 non-patients according to a conventional art.

FIGS. 3a to 3f represent information about CRC patients of the basic set.

FIGS. 4a to 4c represent information about non-CRC patients of the basic set.

FIGS. 5a to 5f represent information about CRC patients of validation set B.

FIGS. 6a to 6b represent information about non-CRC patients of validation set B.

FIG. 7 represents I information about rectal cancer patients of the CRC patient of validation set B.

BEST MODE

1. Terminology

Figure 1:
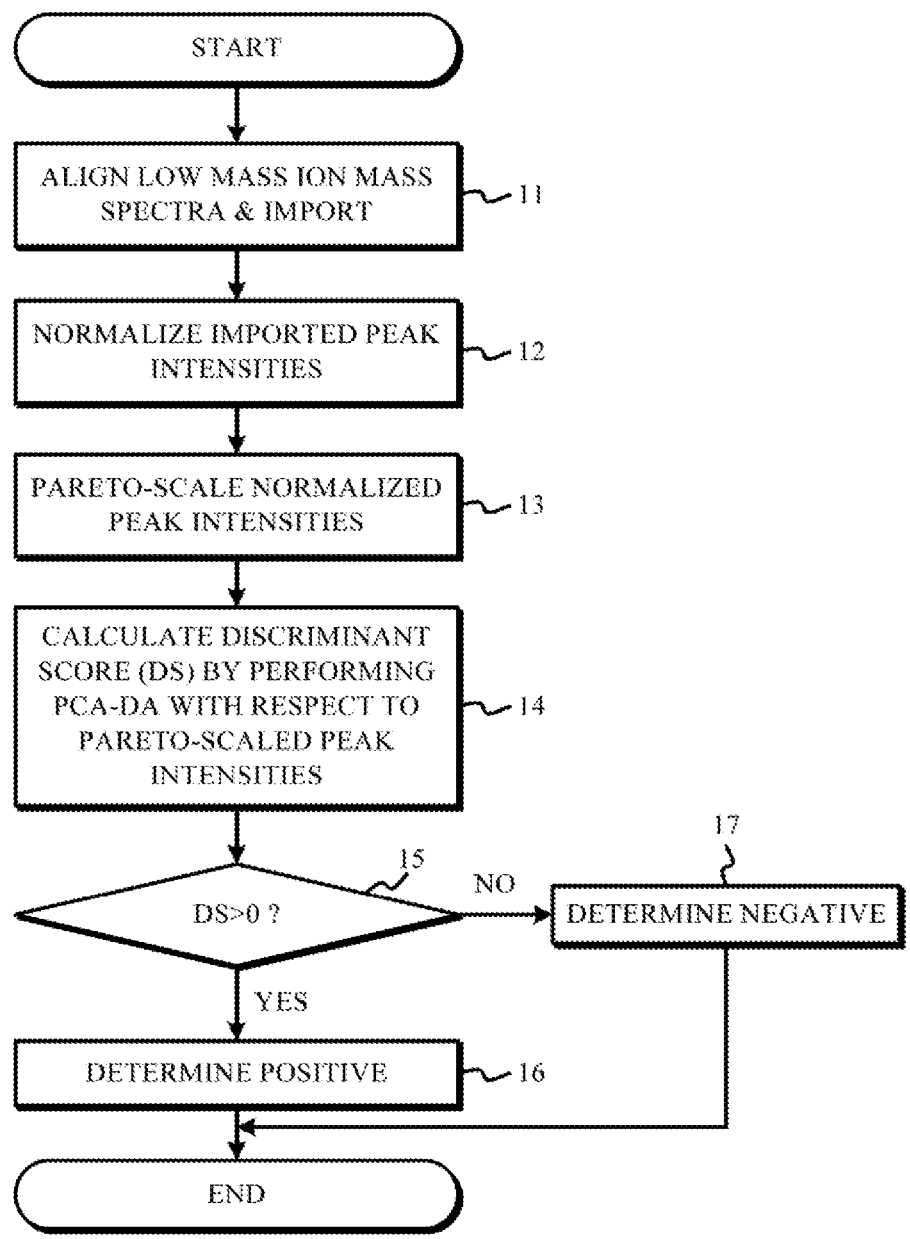
FIGS. 1 to 2 are views provided to explain background art.

As used herein, the "biological sample" may include, but not limited thereto, samples such as whole blood, serum, plasma, urine, excrements, sputum, saliva, tissues, cells, cell extracts, or in vitro cell culture. In the following embodiments, the serums of the CRC patients or non-patients were used as the biological samples.

As used herein, the "intensity" refers to a value obtained by MALDI-TOF mass spectrometer, which is in correlation with the amount of mass ions corresponding to peaks.

As used herein, the "normalization" refers to matching data ranges or making distribution to conformity. The normalization may utilize mean value, median, etc., but not limited thereto. Accordingly, various known normalization methods may be applied. In one embodiment, the normalization may include obtaining a subtotal of intensities of each sample and averaging the same, and multiplying each peak intensity by a multiplying factor so that the subtotal of the intensities of each sample conforms to the obtained mean value. After such normalization, the subtotals of intensities of the respective samples become uniform.

In one embodiment, the "Pareto scaling" refers to subtracting the mean value of each mass from the respective normalized peak intensities, and dividing by square root of the standard deviation. While autoscaling, which is more general version of the scaling, completely offsets the data size information by dividing by the standard deviation, the Pareto scaling provides advantageous effect of avoiding noise amplification by partially maintaining the data size information.

As used herein, the "weight" refers to a factor to adjust the numerical size of the data after multiplication by weight to a proportional relationship with the importance from the statistical viewpoint, as may be exemplified by factor loadings of each peak acquired as a result of principle component analysis (PCA)-based linear discriminant analysis (LDA) in the examples explained below.

As used herein, the "low mass ion" refers to ions with less than 1500 m/s mass value when acquired by MALDI-TOF spectrometry or the like.

As used herein, the mass value measured by the MALDI-TOF mass spectrometer may contain error range of "±0.1 m/z". This is in consideration of the fact that a certain error may be generated depending on environments of the experiment. By way of example, the mass value of 86.1 m/z as indicated in the claims may be understood to actually referring to a range of 86.0 m/z and 86.2 m/z. The error range may be "±0.5 m/z" depending on environments of the experiment.

As used herein, it should be noted that the mass value measured by the MALDI-TOF mass spectrometer is the one acquired in a positive mode of the MALDI-TOF mass spectrometer.

As used herein, the code of the weighting vector may be determined to be positive if the discriminant score is positive, while it is determined to be negative if the discriminant score is negative. The factor loading vector in the PCA corresponds to eigenvector whose code may be randomly decided. That is, mathematically, the values are considered equal according to the eigenvalue problem, even when the computed factor loadings per mass ions are multiplied by −1 and thus change code. However, the negative value of discriminant score is considered to indicate positivity, while the positive value of the discriminant score is considered to indicate negativity. Although the code of the eigenvector is adjusted in the embodiments so that the positive discriminant score indicates negativity and the negative discriminant score indicates positivity, the scope of the invention is not limited to the specific example.

The invention will be explained in greater detail below with reference to Examples. However, the Examples are given only for illustrative purpose, and accordingly, the scope of the present invention should not be construed as limited by any of specific Examples.

2 Examples (1) Sample Preparation

Subjects for Serum Collection

Sera were collected from 133 CRC patients and 153 non-CRC patients. The subjects are the same as those described in the technical background of the invention. Mass spectra measured once from the sera of 286 subjects were used as "basic set" so that a training set was constructed with subset of the basic set, and then preliminary discriminant was acquired via biostatistical analysis on the training set. Further, robustness of discriminant candidates was verified based on the "validation set A" of mass spectra of 5-times additional repetitious measures on the sera of the 286 subjects. The information on the CRC patients of this set is provided in FIGS. 3a to 3f, and the information on the non-CRC patients of the set is provided in FIGS. 4a to 4c.

In addition, sera were collected from new set independent from the basic set, consisting of 144 CRC patients and 100 non-CRC patients. This set will be referred herein as "validation set B". The information on the CRC patients of this set is provided in FIGS. 5a to 5f, and the information on the non-CRC patients of the set is provided in FIGS. 6a to 6b.

Among the CRC patients of the validation set B, 44 were locally advanced rectal cancer (LARC) patients, whose sera were collected before chemoradiotherapy (CRT) The patients received 50.4 GY/28 FX of radiotherapy, combined with pharmacological treatment with tegafur/uracil (400 mg/m$^2$/day) and leucovorin (90 mg/day) for seven days. FIG. 7 shows tumor regression grade, from which it is possible to construct a responsive patient set which responds to the treatment and a non-responsive patient set which does not. From the patient sets, low mass ions to predict patient's individual responsivity to a specific treatment can be determined, and it is thus possible to provide information to predict patient's individual responsivity to a specific treatment by utilizing the low mass ions to predict the responsivity to the treatment.

The total 253 non-CRC patients from the validation sets A and B are the volunteers to the health medical checkup program hosted by the Korean National Cancer Center. For the purpose of diagnosis and judgment of stages and range of diseases, all the CRC patients went through necessary tests including biopsy, colomoscopy, and computed tomography (CT) scan on abdomen and pelvic area F-18 deoxyfluoroglucose positron emission tomography (FDGPET) was performed when needed.

(2) Sample Preparation

Serum Preparation and Mass Spectrometry

Four-fold the volume of methanol/chloroform (2:1, V/V) was rigorously mixed with 25 µl serum and incubated at room temperature for 10 minutes. The mixture was centrifuged at 4° C. for 10 minutes, 6000×g. The supernatant was completely dried in a concentrator for 1 hour and dissolved in a vortexer in 30 µl of 50% acetonitrile/0.1% trifluoroacetic acid (TFA) for 30 min.

Methanol/chloroform extract was mixed in 50% acetonitrile/0.1% TFA with a-cyano-4-hydroxycinnamic acid solution (1:12, v/v), and 1 µl mixture was placed on the MALDI-target. The mass spectra of the serum extracts from the patients and non-patients were measured using Proteomics Analyzer (Applied Biosystems, Foster City, Calif., USA).

The mass spectral data for one sample is extracted as an mean value of the spectra by 20-times repetitive measures. The mass value interval of all the individual samples was adjusted so that the maximum mass value was approximately 2500 m/z. To minimize empirical error, various factors including focus mass, laser intensity, target plate, and data acquisition time were checked. The focus mass and laser intensity were desirably fixed at 500 m/z and 5000, respectively. The samples of the validation set were measured five times repetitiously, at the fixed focus mass and laser intensity and with varying target and data acquisition time.

Through this process, the low mass ion mass spectra were extracted from the serum samples using MALDI-TOF mass spectrometry.

(3) Construction of Preliminary Discriminant

Conventionally, as explained above in the technical background of the invention, the discriminant scores (DS) were calculated using all the peaks considered in the principle component analysis-based linear discriminant analysis (PCA-DA). Unlike the conventional cases, the present invention constructs a preliminary discriminant which uses only the peaks with higher contribution to the discriminant scores, to thus draw a discriminant with robust discrimination performance. As used herein, the term "preliminary discriminant" refers to an intermediate discriminant in the process of drawing a final intended discriminant, and the low mass ions constructing the preliminary discriminant are the "preliminary candidate group" of the low mass ions for CRC diagnosis.

By reference to FIG. 8, a method for constructing a preliminary discriminant will be explained below. The process of constructing the preliminary discriminant may be largely divided into two loops, i.e., the first loop of steps 111 to 117 and the second loop of steps 118 to 122.

First, through the first loop, a training set with predetermined sensitivity and specificity is screened. In one embodiment, the predetermined sensitivity and specificity are 100%, respectively.

Figure 8:
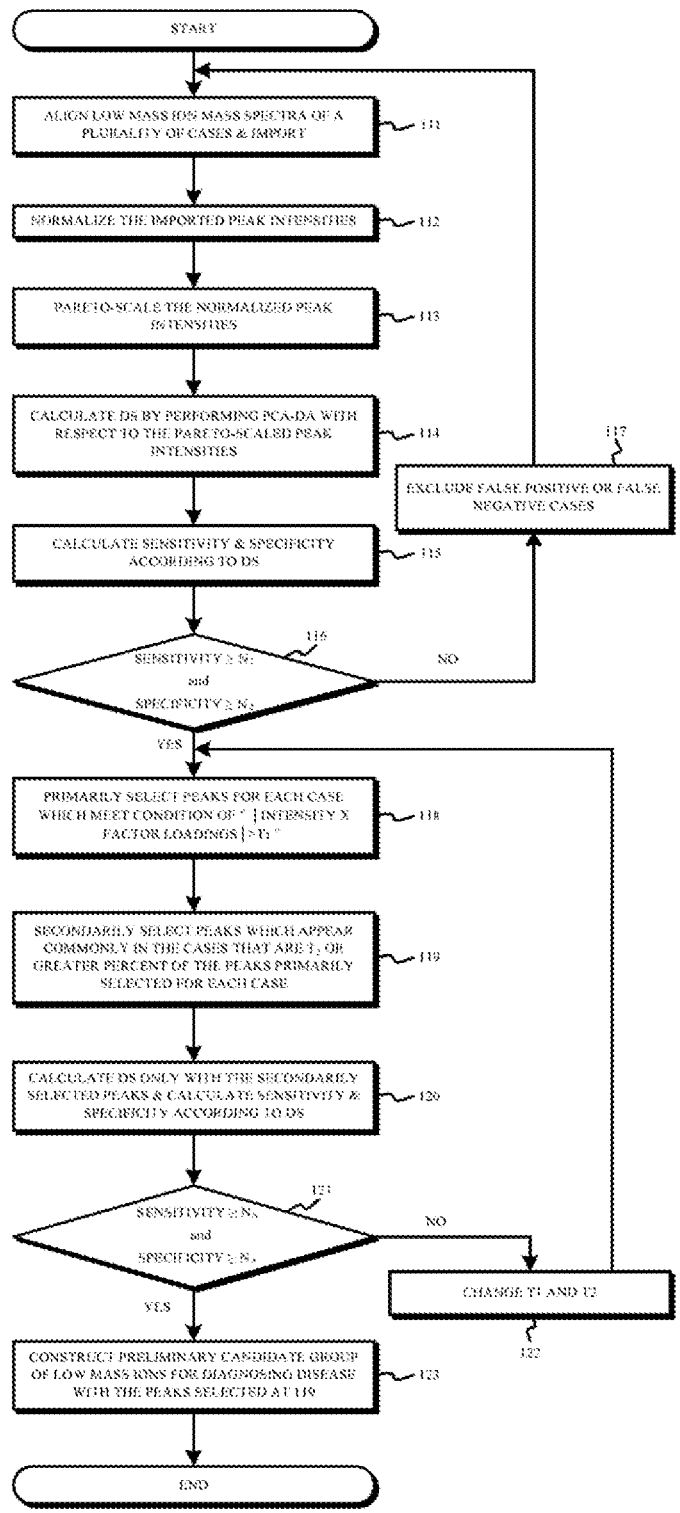
FIG. 8 is a flowchart provided to explain a process of constructing a preliminary discriminant according to the present invention.

The steps 111 to 114 of FIG. 8 are identical to those described in the technical background of the invention. Accordingly, low mass ion mass spectra of a plurality of cases within the basic set were aligned and imported (111), the imported peak intensities were normalized (1122), the normalized peak intensities were Pareto-scaled (113), and the Pareto-scaled peak intensities were biostatistically analyzed and discriminant scores were calculated (114). While it is possible to select any of a variety of biostatistical analysis to calculate the discriminant scores, in one embodiment, the PCA-DA was performed. Sensitivity and specificity were calculated based on the discriminant scores (115), the result of which is provided in FIG. 2 and Table 3 mentioned above.

Figure 2:
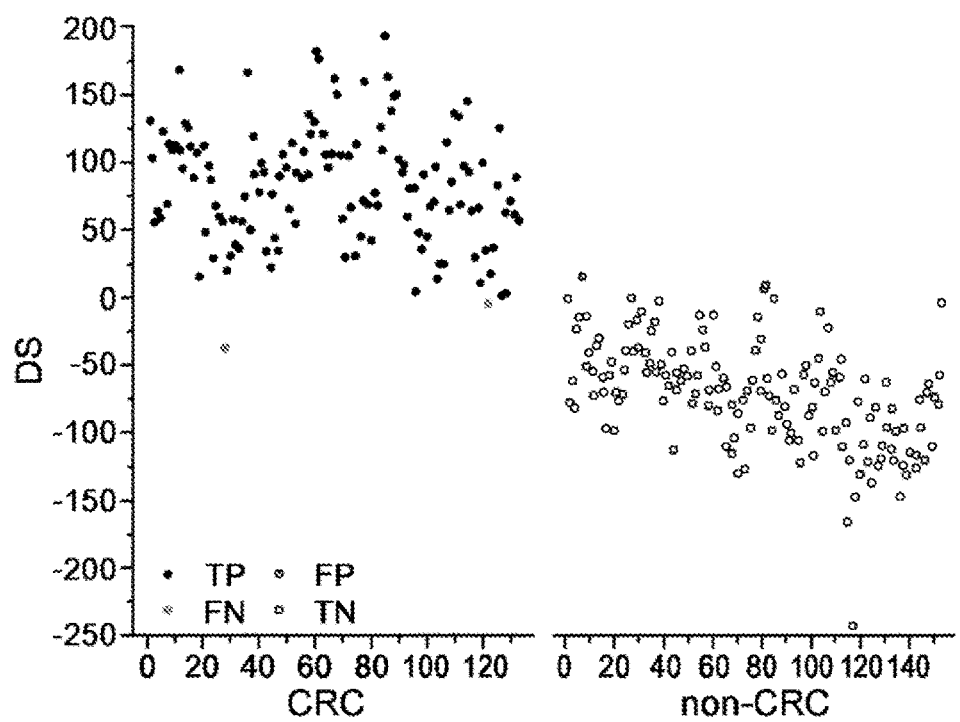
Figure 9:
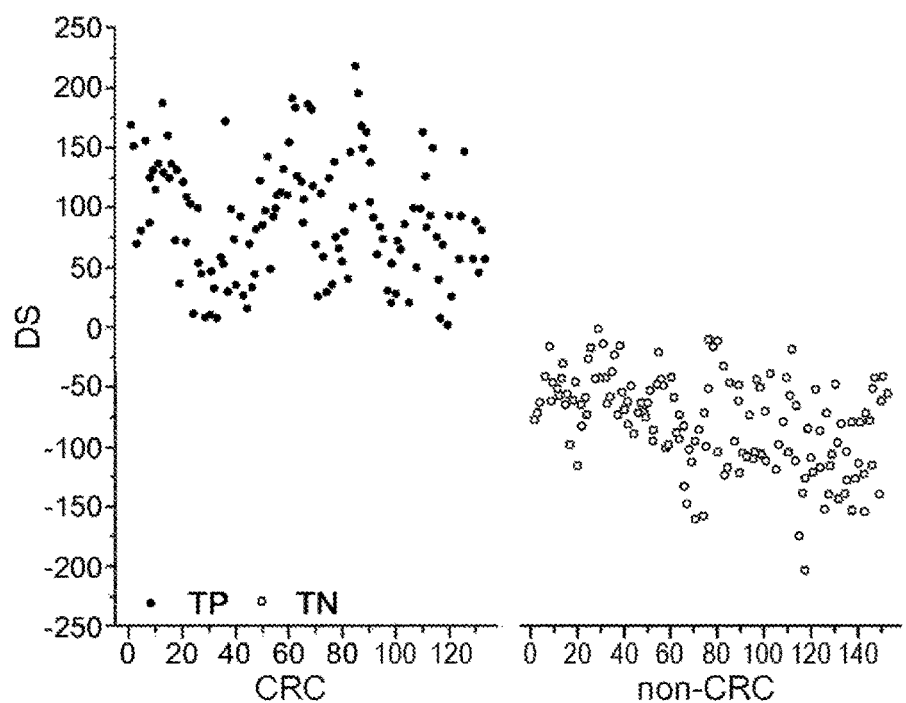
FIG. 9 represents distribution of discriminant scores of the training set cases selected by the first loop from among the two loops to construct a preliminary discriminant.

Although the discrimination result of FIG. 2 and Table 3 is fairly good, the result is short from 100%. Accordingly, a sensitivity threshold $N_1$ and a specificity threshold $N_2$ were set, so that if the sensitivity or the specificity is less than the corresponding threshold, false-positive or false-negative cases were excluded (117). In the present embodiment, both the sensitivity threshold $N_1$ and the specificity threshold $N_2$ were set to 1, so that a training set with both 100% sensitivity and specificity was found. After excluding the two false-positive cases and two false-negative cases of Table 3, steps 111 to 115 were performed again with respect to the resultant set. However, the sensitivity and specificity did not immediately reach 100% upon repeat of steps 111 to 115, but the training set with both 100% sensitivity and specificity was found only when the steps 111 to 117 were repeated several times. The result is shown in FIG. 9 and Table 4.

TABLE 4

| 125 | 0 | 100% |
| 0 | 144 | 100% |
| 100% | 100% | |

Next, by the second loop, predetermined peaks that give considerable influence on the discriminant scores were selected from among 10,000 peaks. As a result, 278 peaks were selected in one embodiment.

Maximum 10,000 peaks were set in the import condition explained above with reference to Table 1. Since sufficient number of samples were imported together, the discriminant constructed by the PCA-DA of MarkerView™ include 10,000 terms. However, in distinguishing CRC patients and non-patients, not all of the 10,000 peaks have the equal degree of significance. Accordingly, by the procedure of the second loop, the peaks that have larger influence on the discriminant scores were selected from among the 10,000 peaks by the two steps. These steps may be referred to as the process of removing unnecessary peaks in the distinguishing of the CRC patients and non-patients from the 10,000 peaks.

From the values of the 10,000 terms, the peaks were primarily selected for the respective cases, if the absolute value of the product of peak intensities multiplied by the factor loadings of the respective peaks exceeds threshold $T_1$ (118). The threshold $T_1$ was 0.1 in one embodiment.

Next, from among the primarily selected peaks for each case, the peaks commonly appearing in the cases exceeding threshold $T_2$ percent from among the training set cases were secondarily selected (119). In one embodiment, the threshold $T_2$ was 50. That is, a preliminary discriminant was constructed only with the peaks that are commonly present in at least 135 cases from among 269 training set cases.

The discriminant scores were calculated only with the peaks selected through the procedure explained above and sensitivity and specificity were accordingly calculated (120). Next, threshold $N_3$ for sensitivity and threshold $N_4$ for specificity were set (121), and if the sensitivity or specificity is less than the corresponding threshold, the threshold was changed to the threshold $T_1$ used at step 118 or to the threshold $T_2$ used at step 119 (122) and then steps 118 to 121 were repeated. In one embodiment, the threshold for sensitivity and the threshold $N_4$ for specificity were 0.9, respectively.

Figure 10:
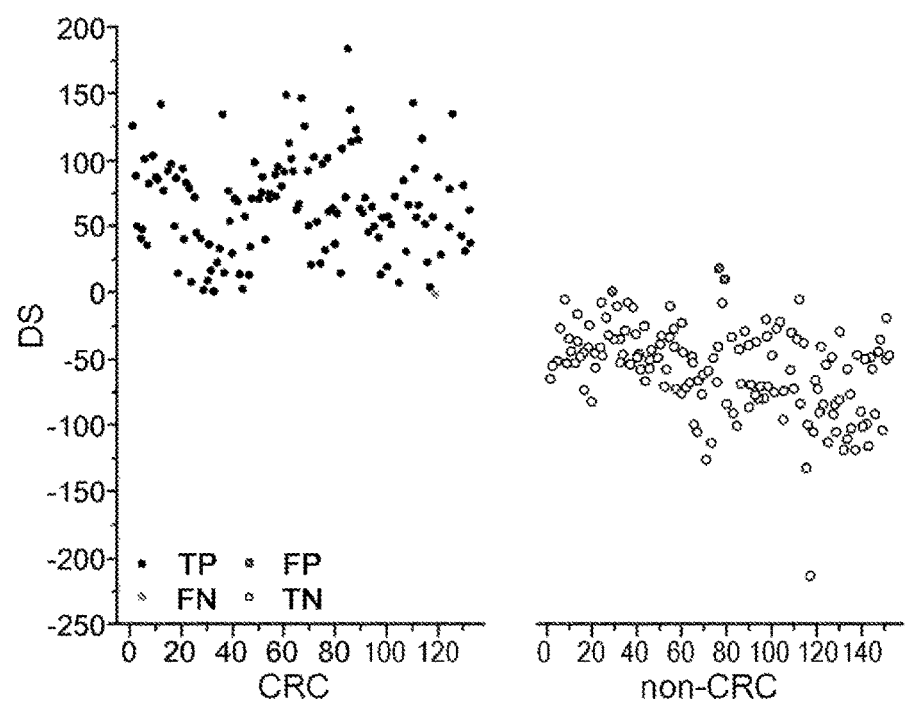
FIG. 10 represents result of discrimination on the training set according to the preliminary discriminant.

Accordingly, a preliminary candidate group of low mass ions for CRC diagnosis was constructed with the peaks that were selected in the procedure explained above (123), and in one embodiment, 278 peaks out of 10,000 peaks were selected. FIG. 10 and Table 5 present the result of discriminating the above-mentioned training set with the preliminary discriminant. While the calculation was done with the peaks that are less than 3% of the entire peaks, the result of discrimination was comparable to the discriminating performance of Table 4 which used the entire peaks. From the above, it was confirmed that not all the 10,000 peaks are necessary to distinguish the CRC patients and the non-patients.

TABLE 5

| 124   | 3     | 97.6% |
|-------|-------|-------|
| 1     | 141   | 99.3% |
| 99.2% | 98.0% |       |

(4) Applying Preliminary Discriminant

The process of applying the constructed discriminant to a sample for discrimination will be explained below. First, MarkerView™ supports function to fulfill the similar purpose. That is, among the sample data imported together, the PCA-DA can be applied on only some of the samples and it is possible to discriminate the samples with the discriminant constructed in that manner. Using this function, it is possible to import the training set and the samples for discrimination together, and hen select only the training set to perform PCA-DA to thus determine how the sample for discrimination is discriminated.

However, while the import process of MarkerView™ is accompanied with the peak alignment function, no function is available to align the peaks of the sample for discrimination in accordance with the training set. Accordingly, the generated training sets are not same, between the peak table (matrix of m/z rows and columns intensities of respective samples) obtained by the importing of the training set, and the peak table obtained by the importing of the training set along with the samples for discrimination. The intensity rows and columns may differ, and m/z values corresponding to the same intensity column also may not always match. Accordingly, to compute discriminant scores by applying the discriminant constructed from the training set on the samples for discrimination, it is necessary that the peak table generated according to input of both the training set and the samples for discrimination is realigned with the peak table generated according to input of the training set only.

The misalignment becomes severer if a plurality of samples for discrimination is imported together with the trainings set. Accordingly, in one embodiment, one more sample for discrimination was added to the training set with respect to all the samples for discrimination and imported, and then realignment, normalization and Pareto-scaling were conducted. This will be explained in detail below with reference to FIG. 11.

First, MarkerView™ does not support the function to align samples to the training set and import. Accordingly, a program was designed, to realign the peak table, which is constructed after importing of the low mass ion mass spectra of the samples for discrimination together with the training set, to the peak table which is constructed after importing of the training set only, so that low mass ion mass spectra of the samples for discrimination which were realigned with the training set were extracted. However, it is more preferable that the samples for discrimination are aligned with the training set from the beginning (i.e., without requiring realignment process) and imported, and it is possible to do so by constructing a program (211) Next, the imported peak intensities were normalized (212) and the normalized peak intensities were Pareto-scaled (213). Next, discriminant scores were calculated from the factor loadings for the respective peaks, which were acquired by the PCA-LDA with respect to the peak intensities and the training set of the Pareto-scaled low mass ions (214). It was then determined whether or not the calculated discriminant score is greater than a cutoff value (S) (125), and if so, it was determined positive (216), while it was determined negative if the calculated score is less than the cutoff value (S) (217). The cutoff value (S) in one embodiment was 0.

Figure 12:
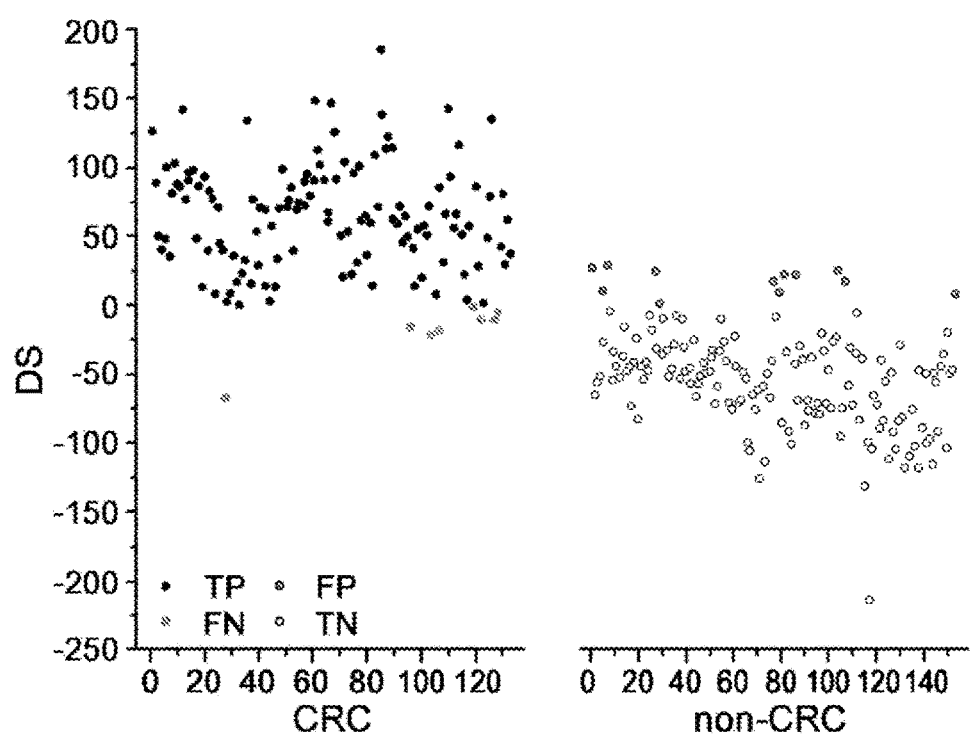
FIG. 12 represents the result of discriminating basic set according to the preliminary discriminant.

The eight CRC patient samples and 9 non-CRC patient samples, which were excluded in the construction of the training set from the basic set, were also processed as explained above. Accordingly, the discriminant score was calculated using the preliminary discriminant and the entire basic set was discriminated. The result is shown in FIG. 12 and Table 6.

TABLE 6

| 125   | 12    | 91.2% |
|-------|-------|-------|
| 8     | 141   | 94.6% |
| 94.0% | 92.2% |       |

Because the cases were already excluded from the process of constructing a discriminant, these were anticipated to be discriminated to be false positive or false negative, and such anticipation was almost correct except for one case which was discriminated to be true positive.

(5) Improvement of Discriminant

In the process of constructing preliminary discriminant, the peaks with greater contribution to the discriminant score were selected from among the 10,000 peaks. However, considering the presence of the peaks that do not generate problem for the training set, but can potentially deteriorate the discrimination performance for the mass spectra re-measured with respect to the same CRC patient or non-CRC patient sera, or for the new CRC patient and non-patient sets, there is a need to actively remove these. In the process of improving discriminant, this step is included before the low mass ions for diagnosing CRC are finally determined.

To validate robustness of a discriminant, repeated measure experiment was conducted with respect to the basic set for 5 times, and the repeated measure experiment was also performed 5 times with respect to the new CRC patient and non-patient sets. These set were named "validation set A" and "validation set B" respectively. It is hardly possible to confirm that the repeated measure of the mass spectrum is always conducted under exactly the same conditions in the processes like vaporization using laser beam, desorption, ionization, or the like, in addition to the process of freezing and thawing the sera and mixing the sera with methanol/chloroform to obtain extract, and it is also hard to rule out introduction of disturbances due to various causes. In other words, the DS with respect to the repeatedly-measured individual mass spectrum may have a predetermined deviation, and considering this, interpretation in one embodiment was made by computing an mean DS with respect to the sample which was repeatedly measured 5 times.

Table 7 provides the result of discriminating the validation sets A and B with the discriminant of 10,000 terms as a result of the conventional technology, i.e., by PCA-LDA by MarkerView™, and Table 8 shows the result of discriminating the validation sets A and B with the preliminary discriminant with 278 terms.

TABLE 7

| Validation Set A | | | Validation Set B | | |
|---|---|---|---|---|---|
| 119 | 65 | 64.7% | 138 | 47 | 74.6% |
| 14 | 88 | 86.3% | 6 | 53 | 89.8% |
| 89.5% | 57.5% | | 95.8% | 53.0% | |

TABLE 8

| Validation Set A | | | Validation Set B | | |
|---|---|---|---|---|---|
| 124 | 60 | 67.4% | 138 | 41 | 77.1% |
| 9 | 93 | 91.2% | 6 | 59 | 90.8% |
| 93.2% | 60.8% | | 95.8% | 59.0% | |

The discriminant consisting of 10,000 mass ions exhibited perfect discrimination performance with respect to the training set, but with reference to Table 7, the specificity was particularly low with respect to validation sets A and B, which in turn had low positive predictive value as well. The preliminary discriminants also exhibited very good discrimination performance (Table 5) with respect to the training set, but the discrimination result with respect to the validation sets (Table 8) was far from satisfaction.

Figure 13:
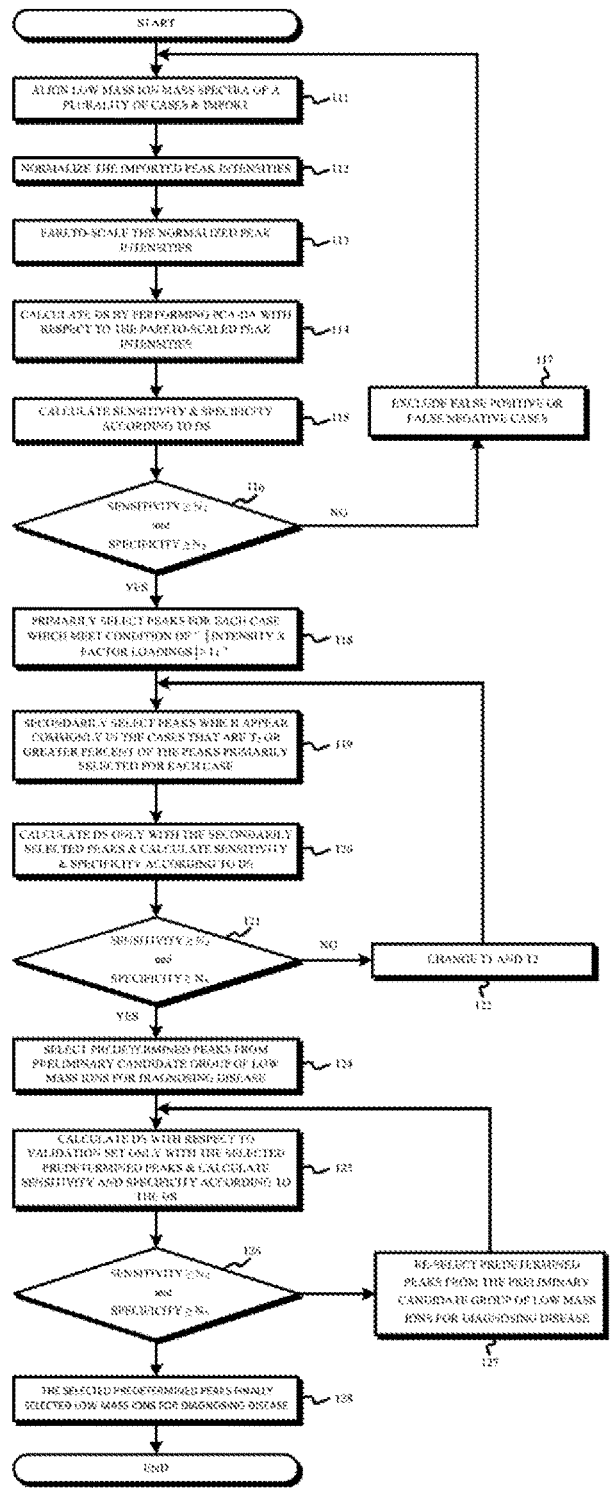
FIG. 13 is a flowchart provided to explain a process of constructing a final discriminant according to the present invention.

Accordingly, in one embodiment of the present invention, the following steps were performed to improve the preliminary discriminant to more robust discriminant. Referring to FIG. 13, steps 111 to 122 identical to those explained above with reference to FIG. 8 were performed, according to which the preliminary candidate group of the low mass ions constructing the preliminary discriminant were selected. Next, predetermined peaks were selected from the preliminary candidate group (124), the DS was calculated with respect to the validation set cases with only the selected predetermined peaks, and sensitivity and specificity were calculated as a result (125). Thresholds $N_5$ and $N_6$ for the sensitivity and the specificity were set, respectively (126), so that if the sensitivity or the specificity was less than the corresponding threshold, peaks were selected against differently from step 124 (127) and steps 125 to 126 were reiterated. In one embodiment, the thresholds $N_5$ and $N_6$ for the sensitivity and the specificity were set to 0.8, respectively. After reiterating the process to improve the result, the mass values of the low mass ions for diagnosing CRC were filially selected (128).

Figure 14A:
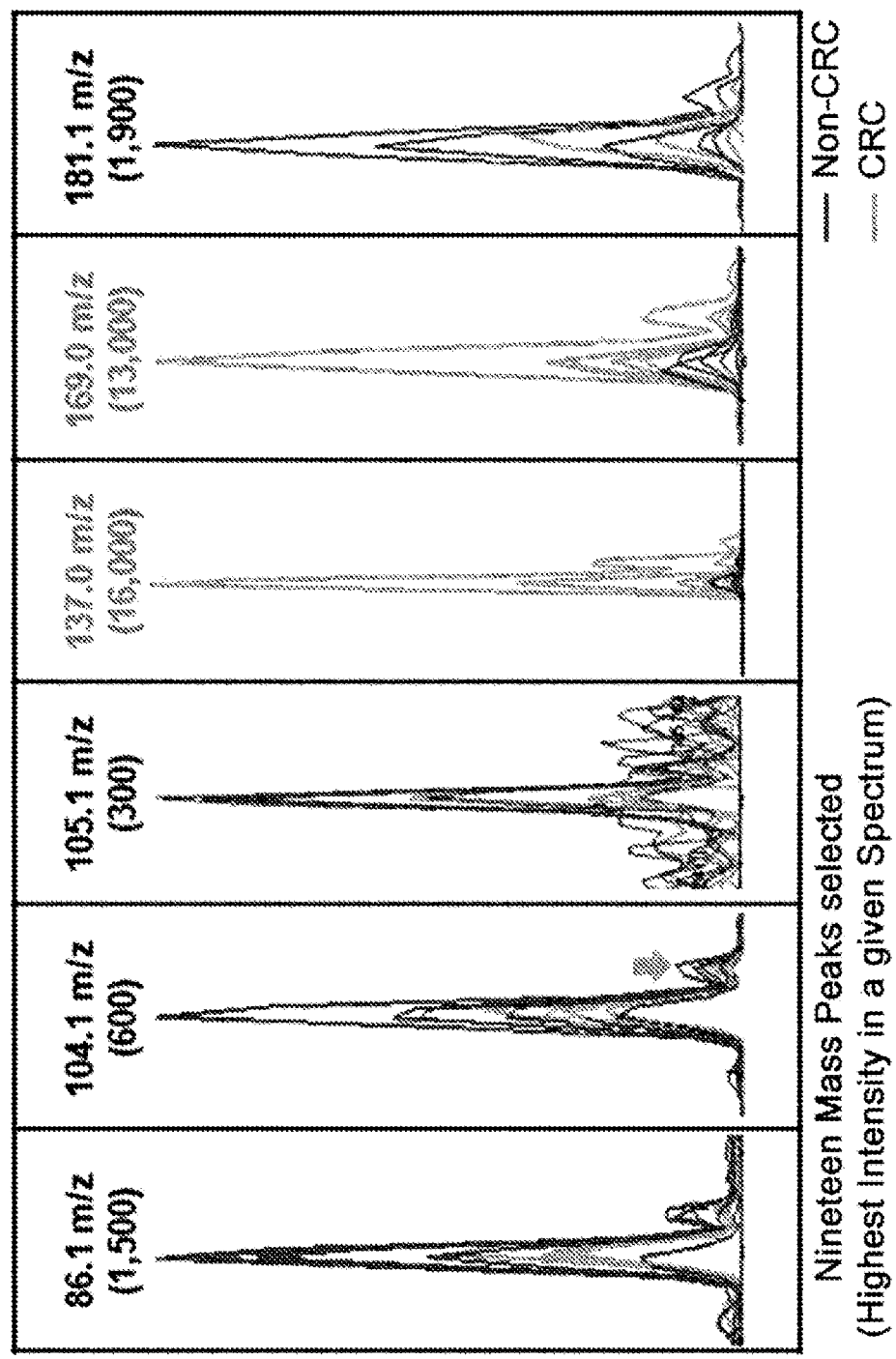
FIGS. 14a to 14c represent peak intensities of the low mass ions for diagnosing CRC as determined according to the method of the present invention.
Figure 14B:
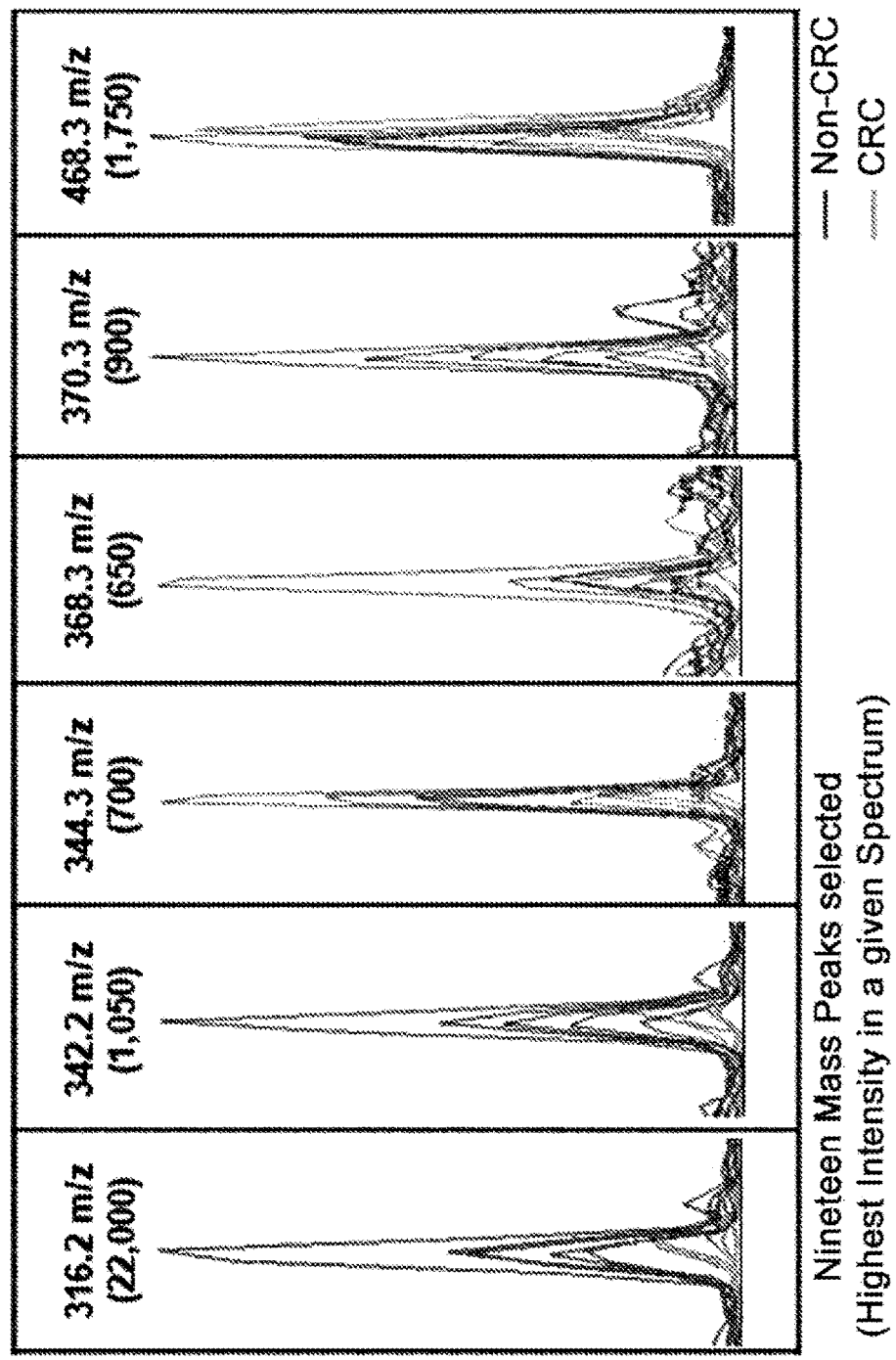
Figure 14C:
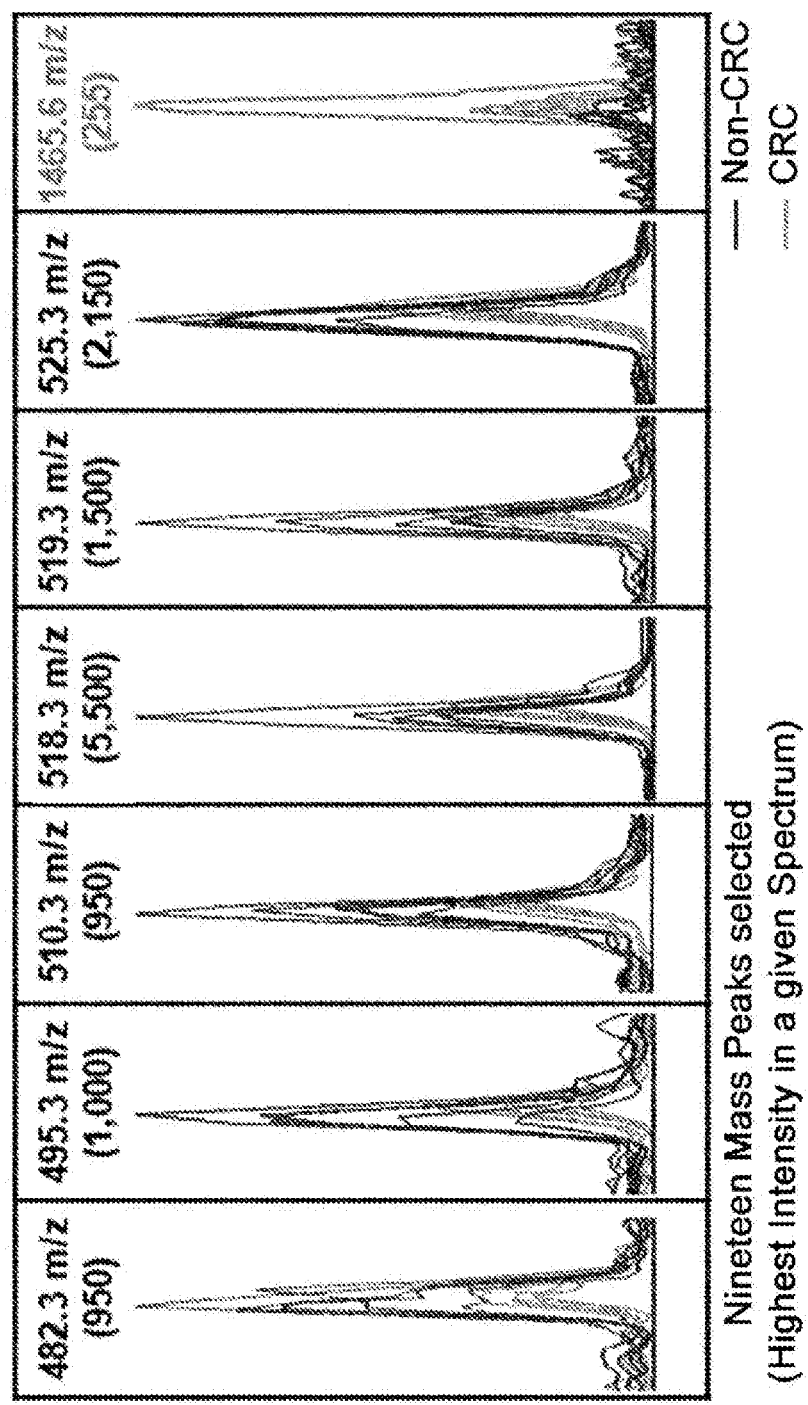

As explained above, in one embodiment, 278 peaks were selected into the preliminary candidate group, peaks were randomly selected from the preliminary candidate group so that the discrimination performance was analyzed. If the discrimination performance does not meet the targeted discrimination performance, peaks were selected against in the manner of deleting or adding some or all the peaks and then the discrimination performance was investigated again. More specifically, the final discriminant was selected with the discriminant that has all the sensitivity, specificity, positive predictive value and negative predictive value for the validation sets A and B exceeding 80%. The final discriminant consists of 19 low mass ions which are referred to as 'low mass ions for CRC diagnosis" and the discriminant finally obtained according to the present invention with the above is referred to as "final discriminant" The mass value of the low mass ions for CRC diagnosis is provided in Table 9, and FIGS. 14a to 14c show the example of the peak intensities of the low mass ions for CRC diagnosis based on the comparison of CRC patients and non-patients. Concerning 137.0, 169.0 and 1465.6 m/z, the peak intensities were relatively higher in the CRC patient sera, while the peak intensities in the non-CRC patients sera were relatively higher concerning the rest 16 low mass ions excluding he above.

TABLE 9

| 86.1 | 104.1 | 105.1 | 137.0 | 169.0 | 181.1 | 316.2 | 342.2 | 344.3 | 368.3 |
|---|---|---|---|---|---|---|---|---|---|
| 370.3 | 468.3 | 482.3 | 498.5 | 510.3 | 518.3 | 519.3 | 525.3 | 1465.6 | — |

(6) Implementation and Analysis of Final Discriminant

Figure 11:
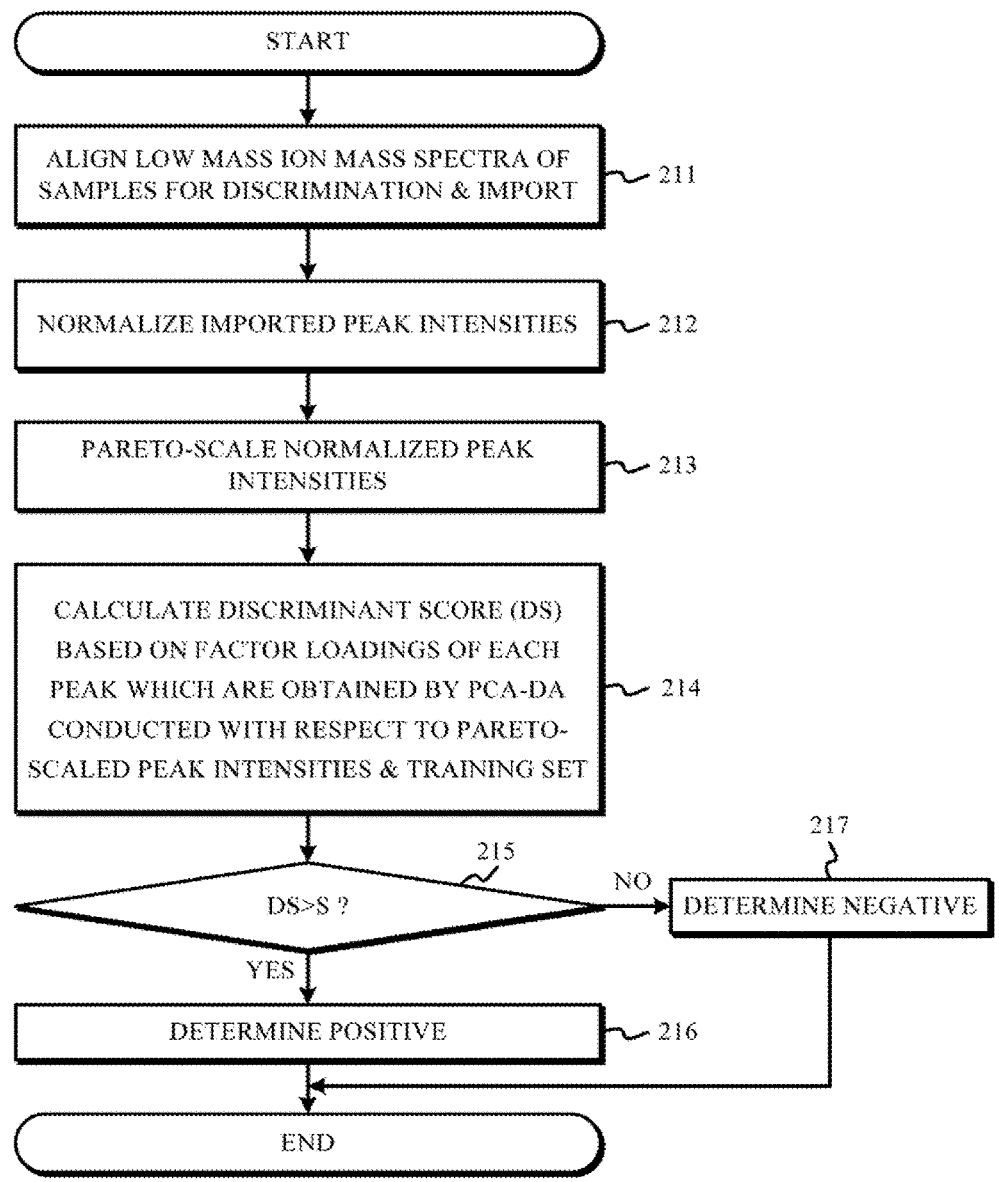
FIG. 11 is a flowchart provided to explain a process of implementing a discriminant on the samples for verification.
Figure 15:
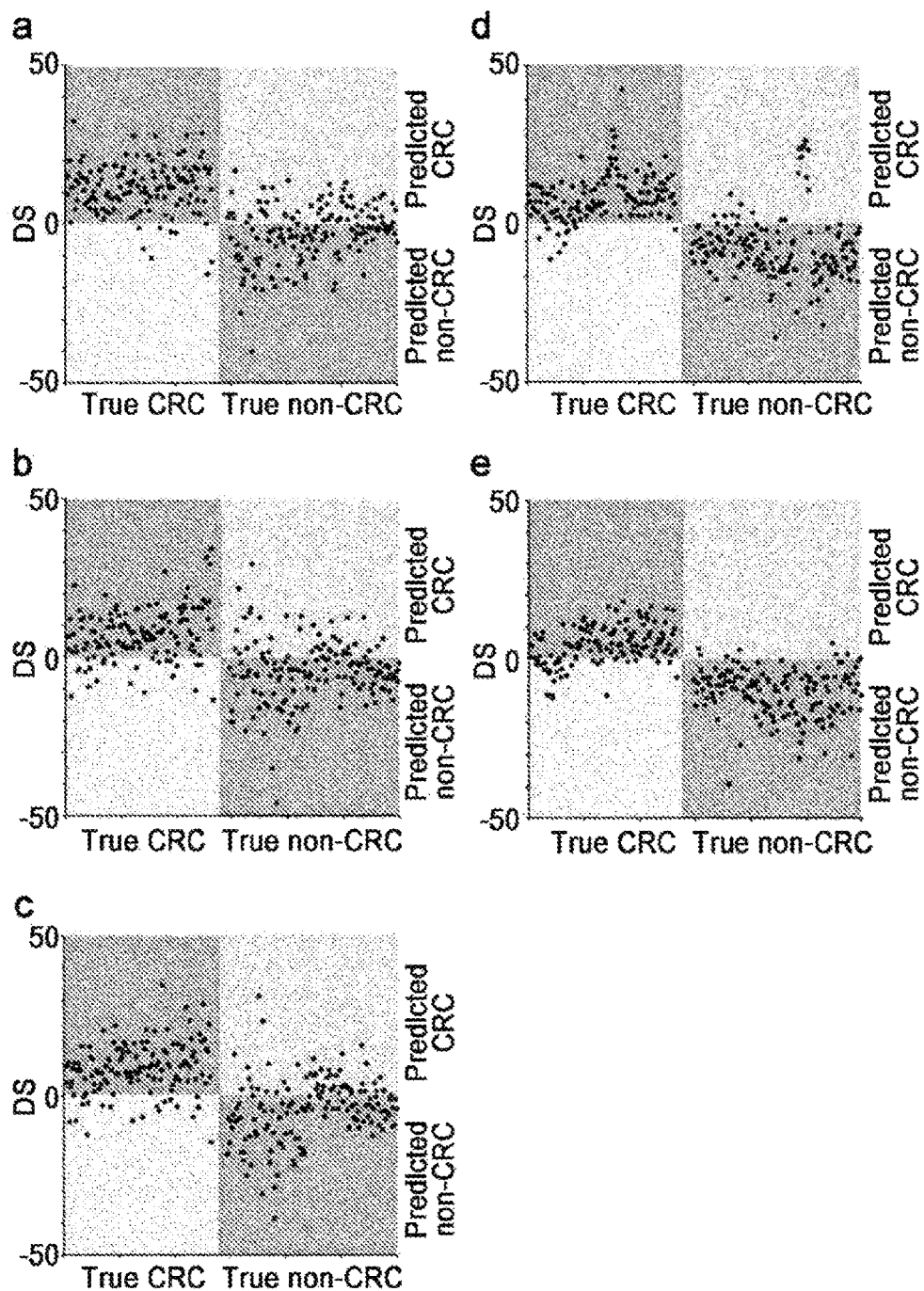
FIG. 15 represents the result of calculating discriminant scores regarding the mass spectra of validation set A repeatedly measured five times according to the final discriminant and discriminating each repeatedly measured set.
Figure 17:
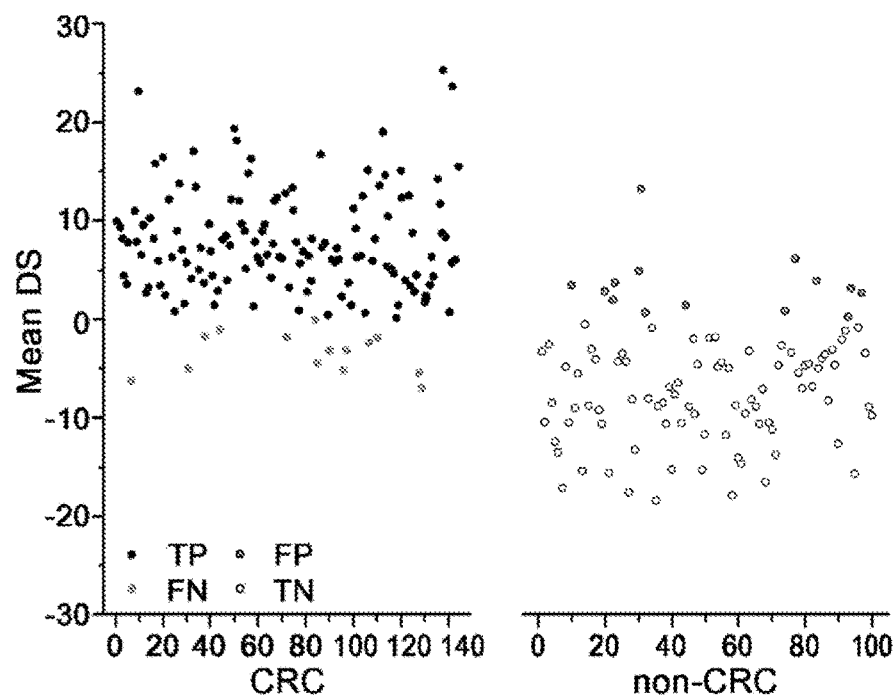
FIG. 17 represents the result of discriminating validation set B which is repeatedly measured five times, by calculating mean DS according to the final discriminant.

The result of discrimination is acquired by implementing the final discriminant utilizing the 19 low mass ions for CRC diagnosis on the samples for discrimination according to the method of FIG. 11. FIGS. 15, 17, 18 and Table 10 provide the result of discrimination by the final discriminant implemented on the validation sets A and B.

Figure 16:
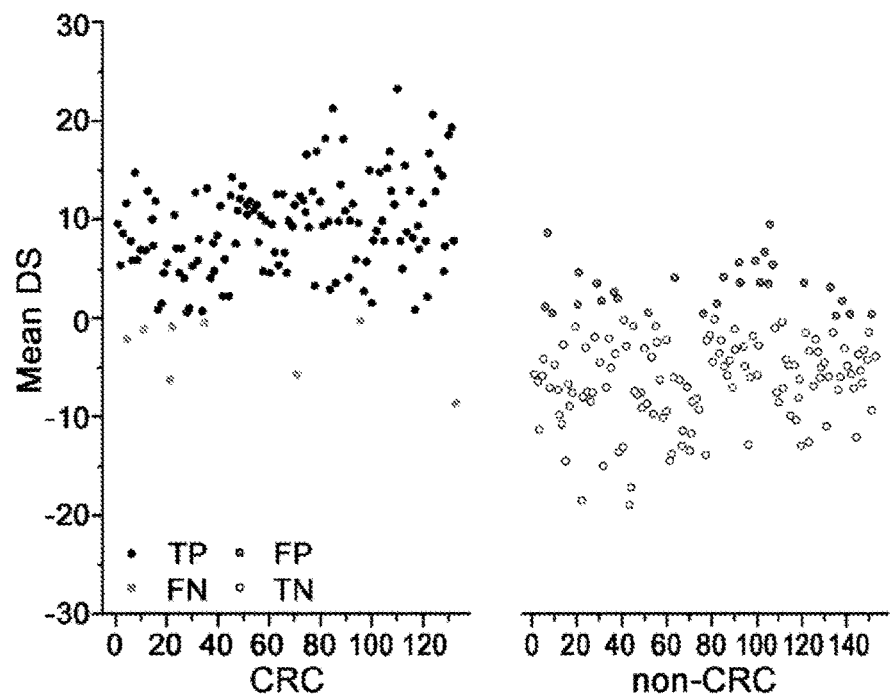
FIG. 16 represents the result of calculating discriminant scores regarding the mass spectra of the validation set A repeatedly measured five times according to the final discriminant and obtaining a mean DS and discriminating accordingly.

FIG. 15 shows the result of calculating discriminant scores according to the final discriminant with respect to the mass spectra repeatedly measured 5 times and discriminating for each of the repeatedly-measured sets, and FIG. 16 shows the result of discriminating based on the mean value of the five DS. FIG. 17 shows the result of discriminating with the mean DS with respect to the validation set B.

TABLE 10

| Validation Set A | | | Validation Set B | | |
|---|---|---|---|---|---|
| 125 | 29 | 81.2% | 130 | 14 | 90.3% |
| 8 | 124 | 93.9% | 14 | 86 | 86.0% |
| 94.0% | 81.0% | | 90.3% | 86.0% | |

It is shown that both the validation sets A and B have 80% or higher sensitivity, specificity, positive predictive value and negative predictive value.

Figure 18A:
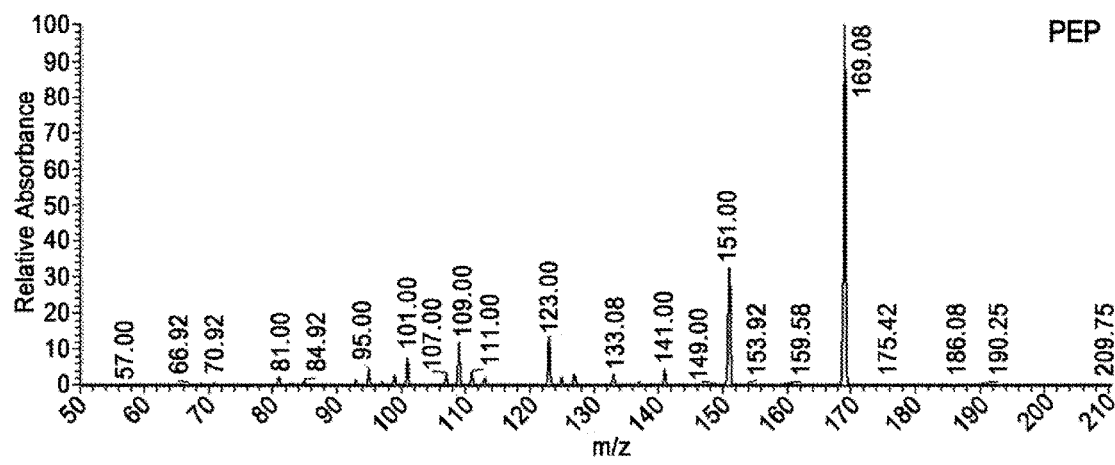
FIGS. 18a to 18b represent the result of characterizing 169.0 m/z from among the 19 CRC low mass ions for CRC diagnosis.
Figure 18B:
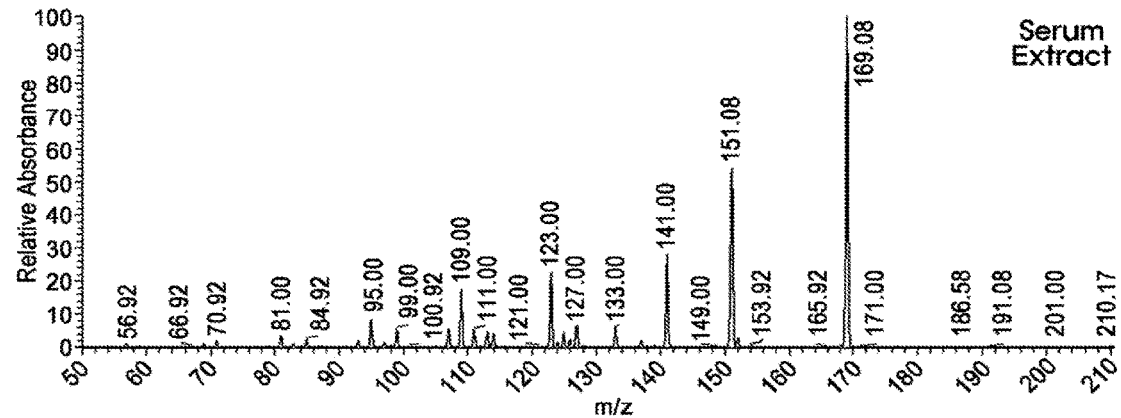
Figure 20:
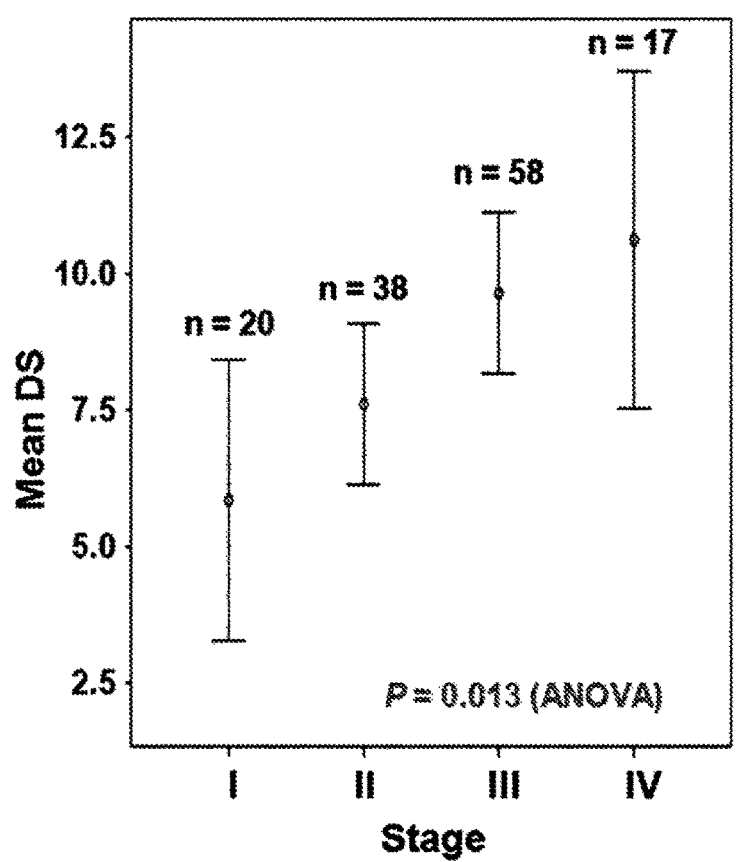
FIG. 20 represents the relationship between the mean DS calculated according to the final discriminant and pathologic parameter.

FIGS. 18a to 18b show the result of characterizing 169.0 m/z from among the 19 CRC low mass ions for CRC diagnosis. FIG. 20 shows MS/MS pattern of 169.0 m/z which is phosphoenolpyruvate. Accordingly, the above indicates the fact that the low mass ions for CRC diagnosis includes phosphoenolpyruvate which is low mass ion.

Figure 19A:
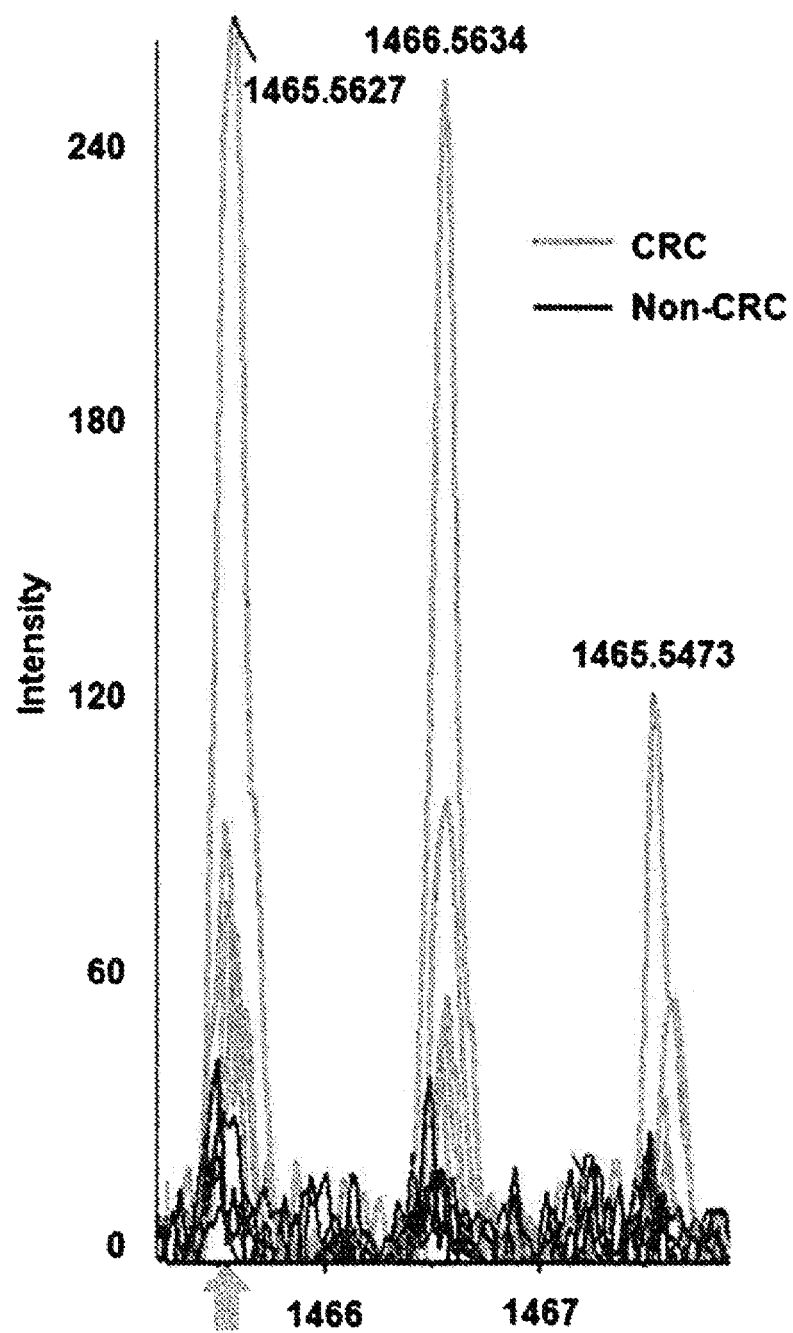
FIGS. 19a to 19c show the result of characterizing 0465.6 m/z from among the 19 CRC low mass ions for CRC diagnosis.
Figure 19B:
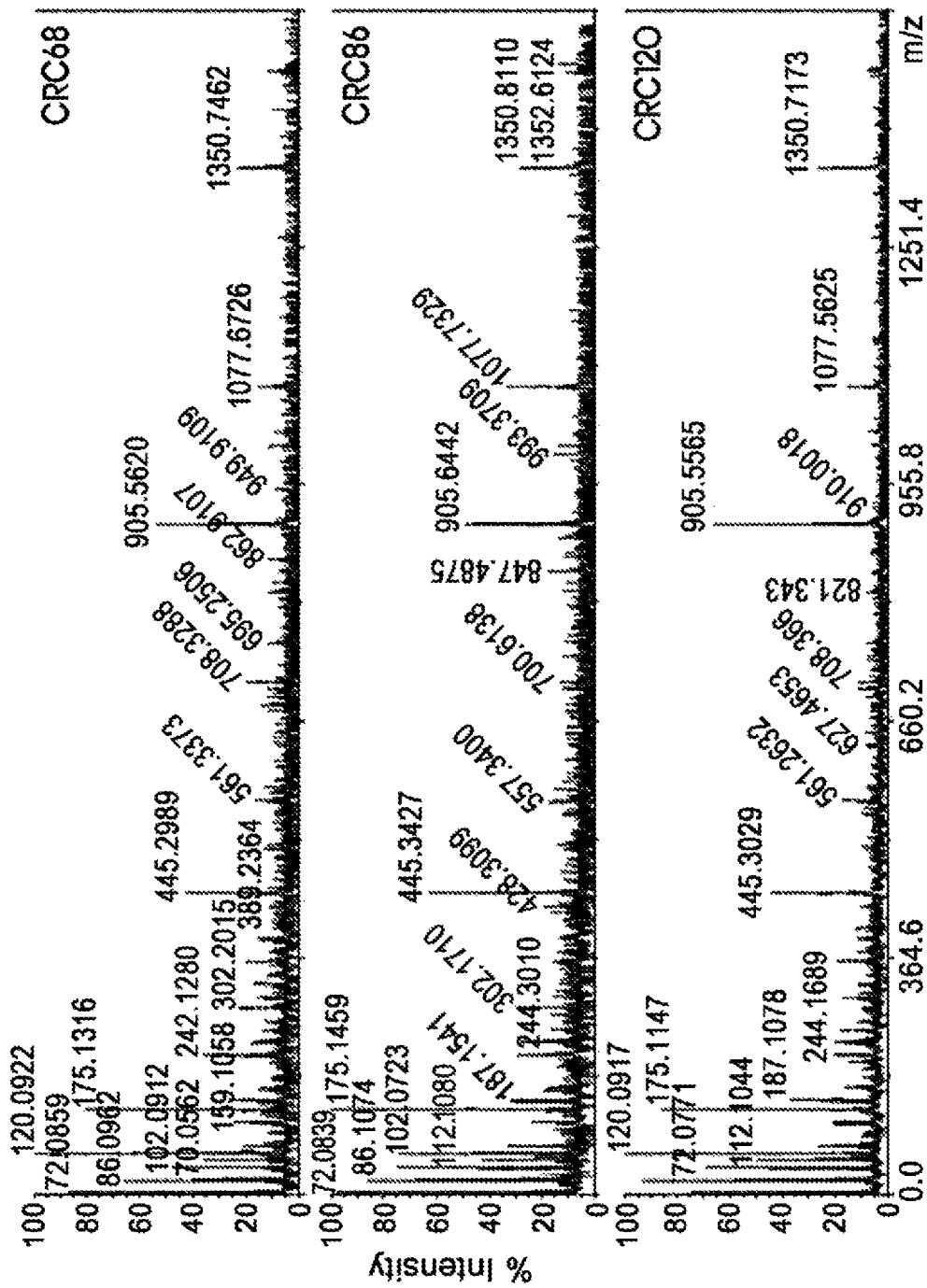
Figure 19C:
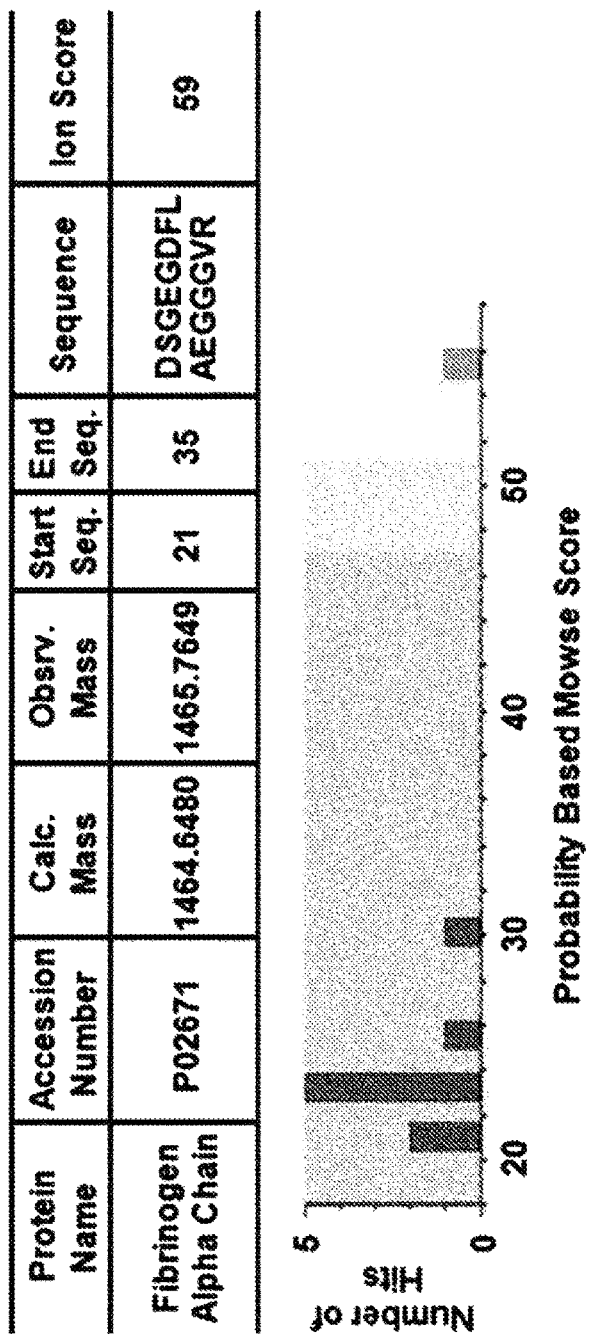

FIGS. 19a to 19c show the result of characterizing 0465.6 m/z from among the 19 CRC low mass ions for CRC diagnosis. (A) represents the peak intensity from the serum extract of the CRC patients relatively higher than the peak intensity of the non-patient sera, (B) represents the MS/MS pattern of 1465.6 m/z of the CRC, and (C) represents the result of characterizing 1465.6 m/z as the fibrinogen alpha chain. These indicate the fact that the low mass ions of fibrinogen or fibrinogen alpha chain is included in the low mass ions for CRC diagnosis.

FIG. 20 represents the relationship between the mean DS and the stage of cancer. Overall, the DS has the increasing tendency as the diseases progresses.

Figure 21A:
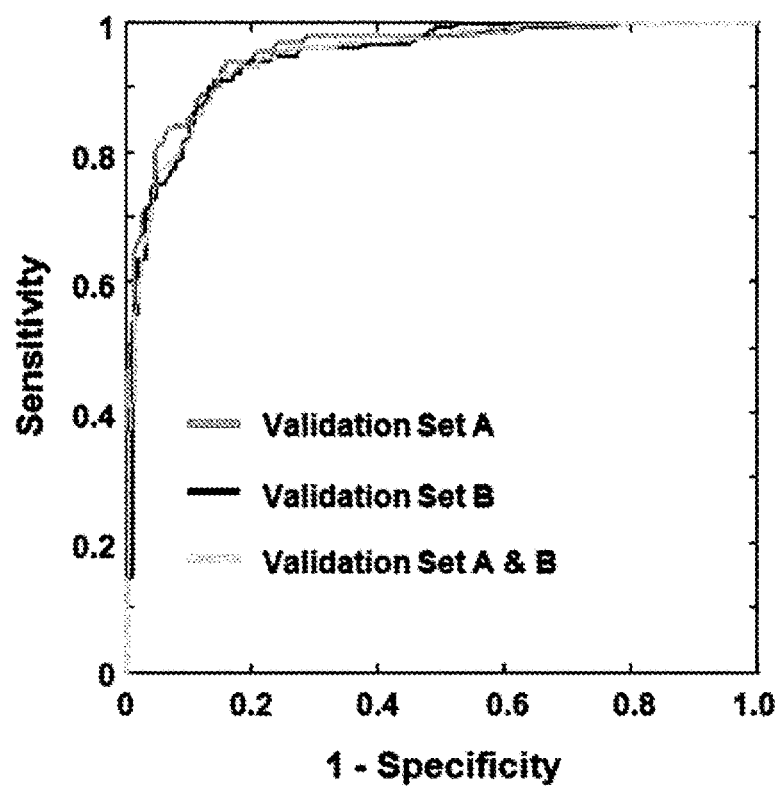
FIGS. 21a to 21b represent the result of discriminating validation sets A and B according to the final discriminant, with the cutoff value S set to 5.5.
Figure 21B:
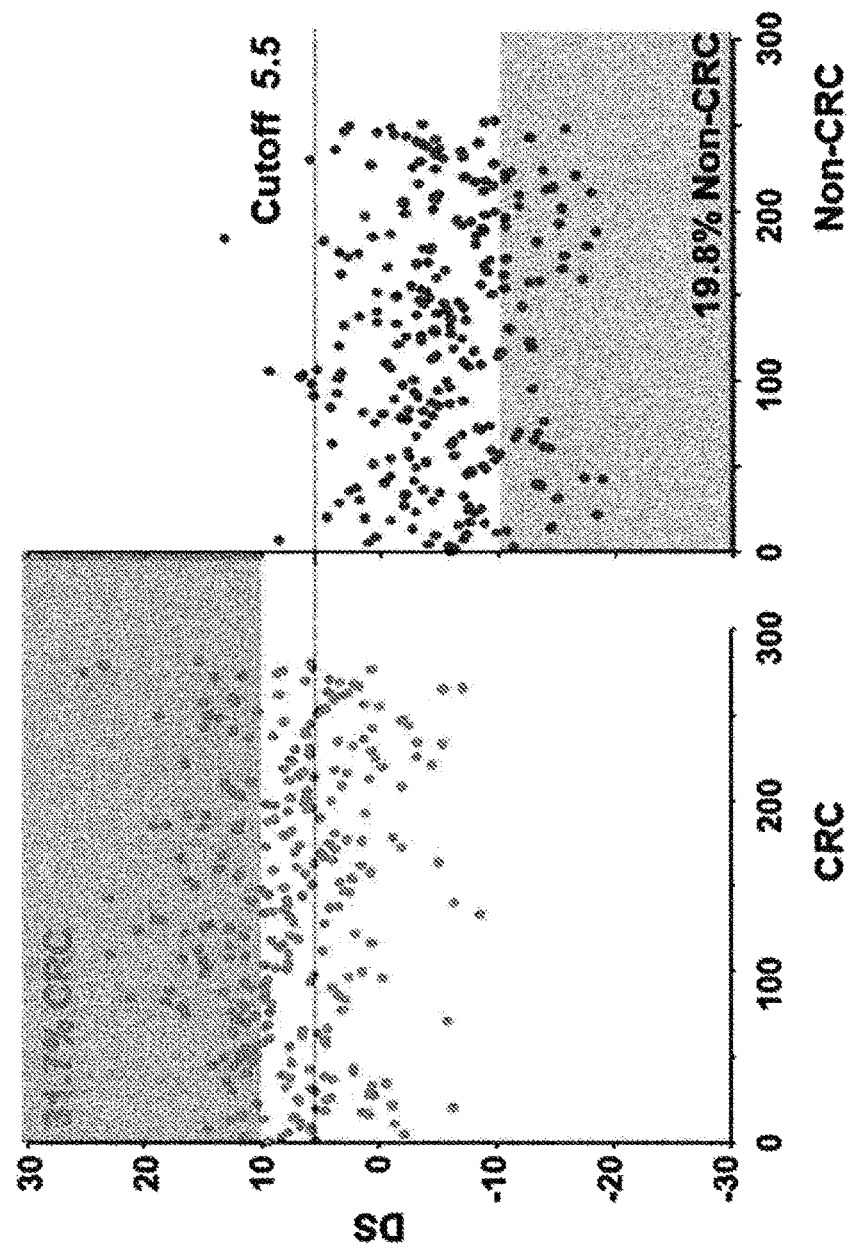

FIGS. 21a to 12b represent the receiver operating characteristic (ROC) curve, showing the discrimination performance obtained when the cutoff value S was set to 5.5 at step 215 of FIG. 11, i.e., when the specificity was increased by compromising the sensitivity. The sensitivity and specificity was comparable to the conventional FOBT analysis, which indicates excellent discrimination performance of the present invention.

Further, it is possible to set the cutoff value S to a first and second cutoff values S and $S_2$ at step 215 of FIG. 11. In this case, it may be determined positive if the DS exceeds the first cutoff value $S_1$ at step 215, or it may be determined negative if DS is less than the second cutoff value $S_2$, or it may be determined on-hold if the DS exceeds the second cutoff value $S_2$ but below the first cutoff value $S_1$. For example, concerning CRC subjects, the first cutoff value S may be set to 10 and the second cutoff value $S_2$ may be set to −10. In this case, better discrimination result can be obtained, because stratified analysis can be conducted in the similar processes as explained above with reference to the embodiments to ensure that the samples determined to be on-hold are discriminated secondarily and more clearly.

The invention claimed is:

1. A method for determining low mass ions for diagnosing colorectal cancer (CRC) in a mammal, the method comprising steps of:
   (a) taking low mass ion mass spectra from a plurality of biological samples of a plurality of mammals wherein the biological samples being prepared by a chemical extracting step, using a mass spectrometer and extracting peak intensities of low mass ions from the low mass ion mass spectra;
   (b) performing a biostatistical analysis on the acquired peak intensities to calculate a discriminant score (DS) for each peak;
   (c) primarily selecting peaks of the respective cases from among the peaks, in which the primarily selected peaks meet a condition that an absolute value of a product of the peak intensities multiplied by factor loadings of the respective peaks exceeds $T_1$;
   (d) secondarily selecting peaks from the primarily selected peaks for the respective cases, in which the secondarily selected peaks are commonly present in the cases which are $T_2$ or greater percent of the training set cases; and
   (e) determining a group of low mass ions for diagnosing CRC with the peaks selected at the step (d)
   wherein
   after the step (d), the discriminant score (DS) is calculated only with the peaks selected at the step (d) so that sensitivity and specificity are calculated according to the calculated DS, and if the calculated sensitivity is less than $N_3$ or if the calculated specificity is less than $N_4$, the $T_1$ and $T_2$ are changed so that the steps (c) and (d).

2. The method as set forth in claim 1, wherein the step (d) comprises a step (d1) of primarily selecting peaks of the respective cases from among the peaks, in which the primarily selected peaks meet a condition that an absolute value of a product of the peak intensities multiplied by factor loadings of the respective peaks exceeds $T_1$.

3. The method as set forth in claim 1, wherein the step (d) further comprises a step (d1) of selecting predetermined peaks from among the peaks selected at the step (d) to calculate DS for validation set cases, calculating sensitivity and specificity according to the calculated DS, and if the calculated sensitivity is less than $N_5$ or if the calculated specificity is less than $N_6$, re-selecting new peaks that are different from the predetermined peaks and reiterating a process of improving discrimination performance with respect to validation set cases and finally selecting mass value of the low mass ions for diagnosing CRC.

4. The method as set forth in claim 3, wherein the low mass ions for diagnosing CRC comprise low mass ions of fibrinogen or fibrinogen alpha chain.

5. The method as set forth in claim 3, wherein the low mass ions for diagnosing CRC comprises low mass ions of phosphoenolpyruvate (PEP).

6. The method as set forth in claim 1, wherein the step (c) comprises:
   a step (c1) of calculating sensitivity and specificity according to the calculated DS;
   a step (c2) of excluding false positive or false negative cases from the plurality of cases, if the sensitivity is less than $N_1$ or if the specificity is less than $N_2$, and reiterating the steps (a) to (b); and
   a step (c3) of selecting the cases as the predetermined training set cases if the sensitivity is equal to or greater than $N_1$ and if the specificity is equal to or greater than $N_2$.

7. The method as set forth in claim 1, wherein the step (a) comprises a step (a1) of aligning low mass ion mass spectra acquired from the biological samples of the plurality of cases and importing.

8. The method as set forth in claim 1, wherein the step (b) comprises:
   a step (b1) of normalizing the imported peak intensities;
   a step (b2) of scaling the normalized peak intensities; and
   a step (b3) of calculating the DS by performing a biostatistical analysis on the scaled peak intensities.

9. The method as set forth in claim 8, wherein the scaling is a Pareto scaling.

10. The method as set forth in claim 8, wherein the biostatsitical analysis is a principal component analysis-based linear discriminant analysis (PCA-DA).

11. The method of claim 1, wherein the peak intensities of low mass ions are extracted and the biostatistical analysis is performed with software in a computer.

* * * * *

UNITED STATES PATENT AND TRADEMARK OFFICE
CERTIFICATE OF CORRECTION

PATENT NO.        : 9,640,375 B2
APPLICATION NO.   : 13/816560
DATED             : May 2, 2017
INVENTOR(S)       : Byong Chul Yoo Page 1 of 1

It is certified that error appears in the above-identified patent and that said Letters Patent is hereby corrected as shown below:

On the Title Page

Item (54) and in the Specification, Column 1 Lines 1-5 the title should read:
METHOD FOR DETERMINING LOW MASS IONS FOR DIAGNOSING COLORECTAL CANCER AND METHOD FOR DIAGNOSING COLORECTAL CANCER USING SAME
Not:
METHOD FOR CRYSTALLIZING LOW MASS IONS FOR DIAGNOSING COLORECTAL CANCER AND METHOD FOR DIAGNOSING COLORECTAL CANCER USING SAME Signed and Sealed this
Twelfth Day of June, 2018

Andrei Iancu
*Director of the United States Patent and Trademark Office*